United States Patent
Nelson et al.

(10) Patent No.: US 7,379,179 B2
(45) Date of Patent: May 27, 2008

(54) RAMAN SPECTROSCOPIC METHODS FOR COMPONENT PARTICLE ANALYSIS

(75) Inventors: Matthew P. Nelson, Harrison City, PA (US); Patrick J. Treado, Pittsburgh, PA (US); Jason Attanucci, Pittsburgh, PA (US)

(73) Assignee: Chem Image Corporation, Pittsburgh, PA (US)

( * ) Notice: Subject to any disclaimer, the term of this patent is extended or adjusted under 35 U.S.C. 154(b) by 387 days.

(21) Appl. No.: 11/000,778

(22) Filed: Nov. 30, 2004

(65) Prior Publication Data
US 2006/0001871 A1 Jan. 5, 2006

Related U.S. Application Data

(60) Provisional application No. 60/584,696, filed on Jun. 30, 2004.

(51) Int. Cl.
*G01N 21/44* (2006.01)
(52) U.S. Cl. ............... 356/301; 356/335; 356/336
(58) Field of Classification Search ........ 356/301–303, 356/335–338, 73
See application file for complete search history.

(56) References Cited

U.S. PATENT DOCUMENTS

| | | | | |
|---|---|---|---|---|
| 5,567,628 A | * | 10/1996 | Tarcha et al. ............... 436/525 |
| 5,870,189 A | * | 2/1999 | Uesugi et al. ............... 356/335 |
| 7,039,452 B2 | * | 5/2006 | McClane et al. ........... 600/424 |
| 7,057,732 B2 | * | 6/2006 | Jorgenson et al. .......... 356/445 |
| 7,120,173 B2 | * | 10/2006 | Roques et al. ................. 372/3 |
| 2001/0006416 A1 | * | 7/2001 | Johnson ...................... 356/73 |

OTHER PUBLICATIONS

Vehring et al, THe characterization of fine particles oroginating from an Uncharged aerosol: Size dependence and detection limits for Raman analysis, Abstract, Journal of Aerosol Science, Oct. 1998.*

Cai, Ph.D., et al., "A Novel Approach to Determining Particle Size Distributions of Pharmaceutical Powders by Near Infrared Spectroscopy", American Pharmaceutical Review.

* cited by examiner

*Primary Examiner*—Layla G. Lauchman
(74) *Attorney, Agent, or Firm*—Morgan, Lewis & Bockius LLP

(57) ABSTRACT

The invention relates to methods of assessing one or more geometric properties of a particle of a substance using a Raman spectroscopic property of the substance. The method is useful, for example, for assessing particle sizes and size distributions in mixtures containing both particles of the substance and other materials.

36 Claims, 56 Drawing Sheets
(7 of 56 Drawing Sheet(s) Filed in Color)

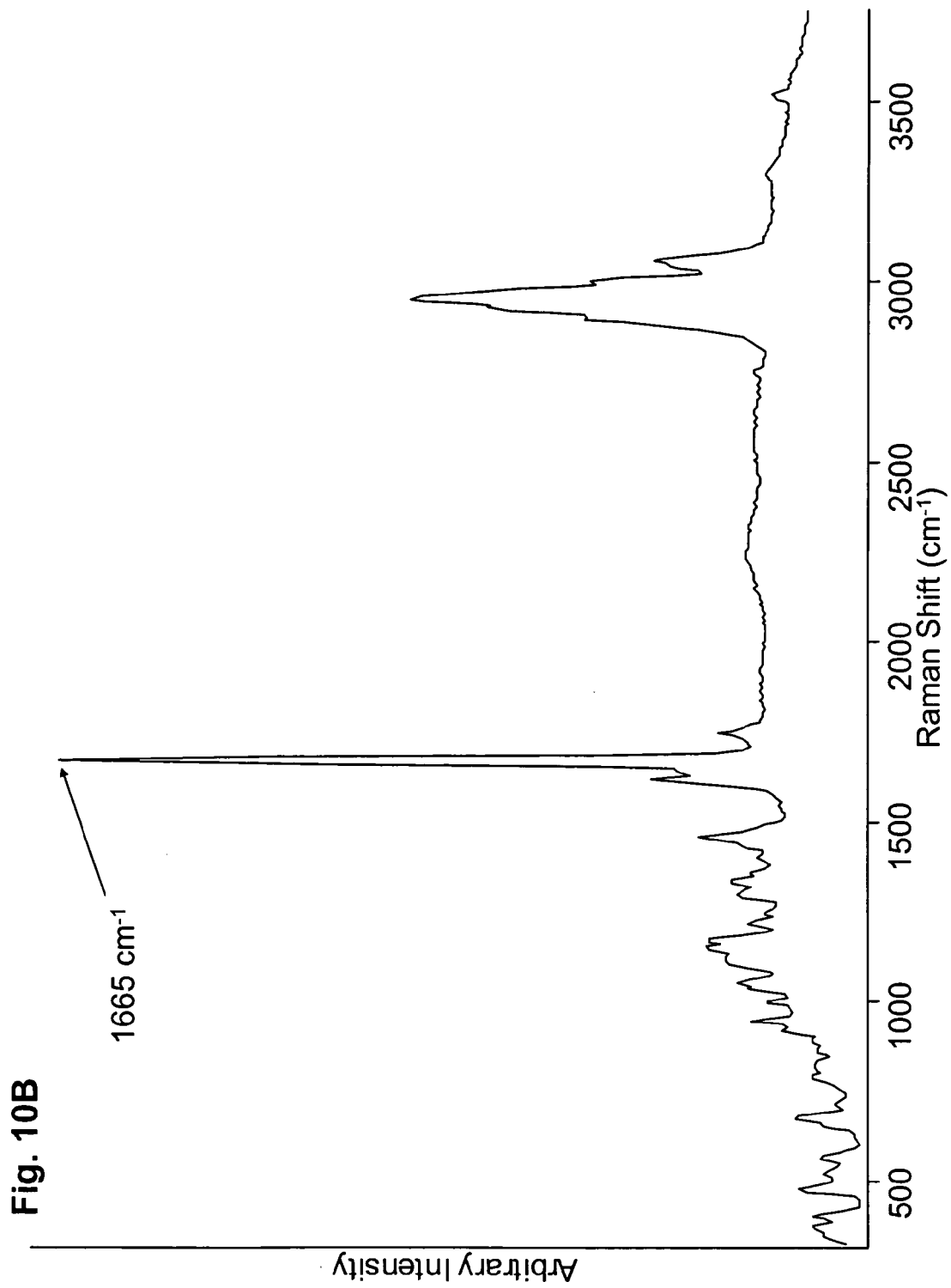

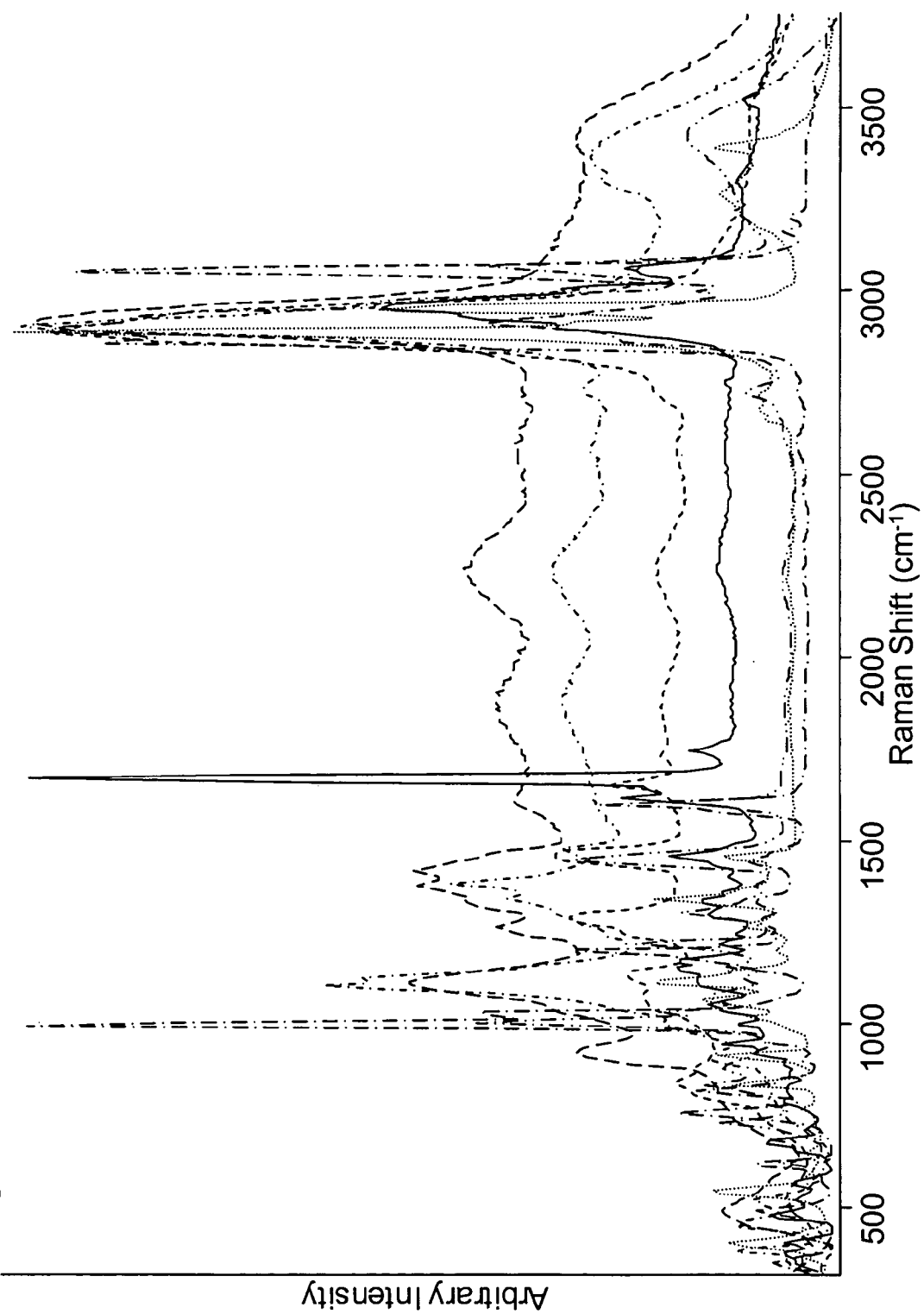

Fig. 12C

| Object | Area (μm²) | Perimeter (μm) | Feret 1 (μm) | Feret 2 (μm) | Max. Chord (μm) | Shape | Aspect |
|---|---|---|---|---|---|---|---|
| 1 | 6.67 | 17.50 | 5.38 | 2.42 | 5.38 | 0.27 | 2.22 |
| 2 | 20.83 | 23.42 | 6.73 | 4.71 | 6.73 | 0.48 | 1.43 |
| 3 | 0.49 | 3.23 | 0.81 | 0.81 | 0.94 | 0.59 | 1.00 |
| 4 | 0.27 | 2.69 | 0.67 | 0.67 | 0.67 | 0.47 | 1.00 |
| 5 | 6.56 | 15.61 | 2.83 | 3.77 | 4.44 | 0.34 | 0.75 |
| 6 | 22.56 | 30.15 | 6.46 | 7.27 | 8.48 | 0.31 | 0.89 |
| 7 | 12.17 | 17.50 | 4.17 | 4.31 | 5.52 | 0.50 | 0.97 |
| 8 | 2.45 | 11.58 | 2.15 | 2.56 | 2.96 | 0.23 | 0.84 |
| 9 | 0.58 | 3.50 | 0.81 | 0.94 | 1.08 | 0.59 | 0.86 |
| 10 | 0.43 | 3.50 | 0.81 | 0.94 | 1.08 | 0.45 | 0.86 |
| 11 | 0.13 | 1.62 | 0.40 | 0.40 | 0.54 | 0.61 | 1.00 |
| 12 | 0.54 | 4.31 | 0.94 | 1.21 | 1.35 | 0.37 | 0.78 |
| 13 | 1.70 | 7.81 | 1.21 | 2.42 | 2.42 | 0.35 | 0.50 |
| 14 | 18.21 | 40.38 | 7.27 | 6.33 | 7.94 | 0.14 | 1.15 |
| 15 | 9.24 | 16.42 | 4.04 | 3.77 | 4.31 | 0.43 | 1.07 |
| 16 | 43.50 | 58.42 | 6.73 | 12.79 | 14.27 | 0.16 | 0.53 |
| 17 | 0.02 | 0.54 | 0.13 | 0.13 | 0.27 | 0.79 | 1.00 |
| 18 | 1.85 | 7.81 | 1.75 | 2.15 | 2.42 | 0.38 | 0.81 |
| 19 | 0.07 | 1.35 | 0.40 | 0.27 | 0.40 | 0.50 | 1.50 |
| 20 | 0.25 | 2.42 | 0.67 | 0.54 | 0.67 | 0.54 | 1.25 |
| 21 | 1.65 | 6.19 | 1.21 | 1.88 | 2.02 | 0.54 | 0.64 |
| 22 | 0.11 | 1.62 | 0.40 | 0.40 | 0.54 | 0.52 | 1.00 |
| 23 | 5.42 | 16.15 | 3.63 | 3.37 | 4.31 | 0.26 | 1.08 |
| 24 | 0.07 | 1.35 | 0.40 | 0.27 | 0.40 | 0.50 | 1.50 |
| 25 | 18.37 | 21.54 | 6.06 | 4.44 | 6.06 | 0.50 | 1.36 |
| 26 | 0.78 | 4.58 | 1.48 | 0.81 | 1.62 | 0.47 | 1.83 |
| 27 | 0.71 | 4.58 | 1.08 | 1.21 | 1.35 | 0.42 | 0.89 |
| 28 | 0.47 | 3.50 | 0.67 | 1.08 | 1.08 | 0.48 | 0.63 |
| 29 | 1.12 | 5.92 | 1.35 | 1.48 | 1.75 | 0.40 | 0.91 |
| 30 | 0.04 | 0.81 | 0.27 | 0.13 | 0.27 | 0.70 | 2.00 |
| 31 | 2.48 | 7.00 | 1.75 | 1.75 | 2.29 | 0.64 | 1.00 |
| Mean | 5.80 | 11.06 | 2.34 | 2.43 | 3.02 | 0.45 | 1.07 |
| Stnd. Dev. | 9.73 | 12.99 | 2.30 | 2.67 | 3.16 | 0.15 | 0.41 |

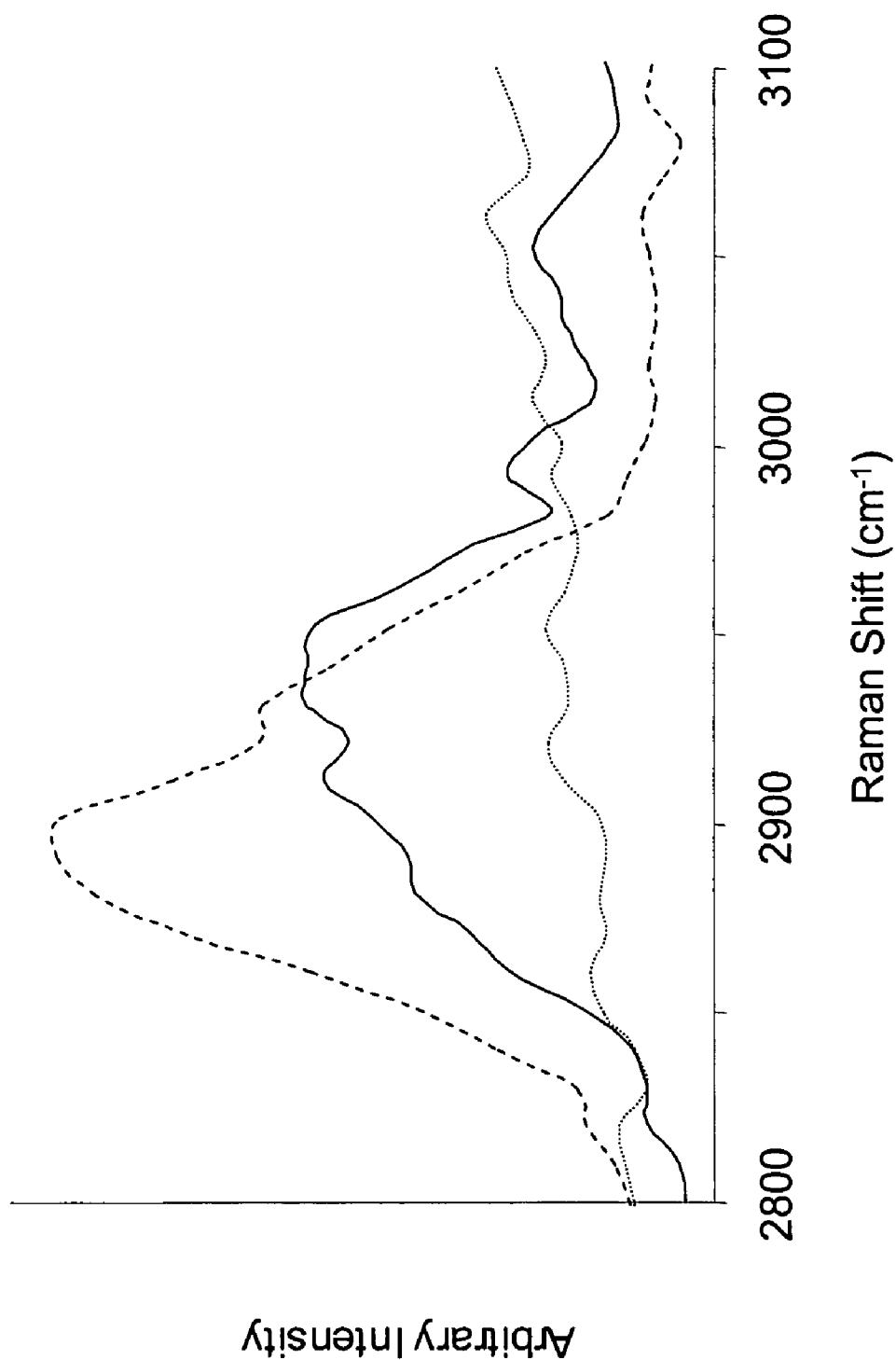

| Object | Area (μm²) | Perimeter (μm) | Feret 1 (μm) | Feret 2 (μm) | Max. Chord (μm) | Shape | Aspect |
|---|---|---|---|---|---|---|---|
| 1 | 21.38 | 21.58 | 6.16 | 4.62 | 7.71 | 0.58 | 1.33 |
| 2 | 2.38 | 6.16 | 1.54 | 1.54 | 3.08 | 0.79 | 1.00 |
| 3 | 30.88 | 24.66 | 6.16 | 6.16 | 7.71 | 0.64 | 1.00 |
| 4 | 2.38 | 6.16 | 1.54 | 1.54 | 3.08 | 0.79 | 1.00 |
| 5 | 21.38 | 21.58 | 4.62 | 6.16 | 6.16 | 0.58 | 0.75 |
| 6 | 14484.56 | 1078.84 | 186.49 | 158.74 | 195.73 | 0.16 | 1.17 |
| 7 | 76.01 | 43.15 | 10.79 | 10.79 | 13.87 | 0.51 | 1.00 |
| Mean | 2091.28 | 171.73 | 31.04 | 27.08 | 33.91 | 0.58 | 1.04 |
| Stnd. Dev. | 5464.98 | 400.19 | 68.62 | 58.14 | 71.45 | 0.21 | 0.18 |

Fig. 15C

| Object | Area (µm²) | Perimeter (µm) | Feret 1 (µm) | Feret 2 (µm) | Max. Chord (µm) | Shape | Aspect |
|---|---|---|---|---|---|---|---|
| 1 | 1496.44 | 197.27 | 47.78 | 50.86 | 61.65 | 0.48 | 0.94 |
| 2 | 187.65 | 64.73 | 16.95 | 15.41 | 18.49 | 0.56 | 1.10 |
| 3 | 978.62 | 191.11 | 58.57 | 29.28 | 58.57 | 0.34 | 2.00 |
| 4 | 147.27 | 64.73 | 13.87 | 18.49 | 20.04 | 0.44 | 0.75 |
| 5 | 624.70 | 126.38 | 38.53 | 21.58 | 38.53 | 0.49 | 1.79 |
| 6 | 323.04 | 80.14 | 20.04 | 20.04 | 24.66 | 0.63 | 1.00 |
| Mean | 626.29 | 120.73 | 32.62 | 25.94 | 36.99 | 0.49 | 1.26 |
| Stnd. Dev. | 528.23 | 61.26 | 18.40 | 13.06 | 19.27 | 0.10 | 0.51 |

Fig. 16C

| Object | Area (μm²) | Perimeter (μm) | Feret 1 (μm) | Feret 2 (μm) | Max. Chord (μm) | Shape | Aspect |
|---|---|---|---|---|---|---|---|
| 1 | 2.00 | 6.00 | 1.00 | 2.00 | 2.00 | 0.70 | 0.50 |
| 2 | 1213.00 | 286.00 | 44.00 | 66.00 | 71.00 | 0.19 | 0.67 |
| 3 | 1.00 | 4.00 | 1.00 | 1.00 | 2.00 | 0.79 | 1.00 |
| 4 | 4860.00 | 412.00 | 56.00 | 119.00 | 120.00 | 0.36 | 0.47 |
| Mean | 1519.00 | 177.00 | 25.50 | 47.00 | 48.75 | 0.51 | 0.66 |
| Stnd. Dev. | 2299.39 | 205.16 | 28.71 | 56.82 | 57.57 | 0.28 | 0.24 |

Fig. 18C

| Object | Area (μm²) | Perimeter (μm) | Feret 1 (μm) | Feret 2 (μm) | Max. Chord (μm) | Shape | Aspect |
|---|---|---|---|---|---|---|---|
| 1 | 94.00 | 50.00 | 13.00 | 12.00 | 14.00 | 0.47 | 1.08 |
| 2 | 7.00 | 12.00 | 3.00 | 3.00 | 3.00 | 0.61 | 1.00 |
| 3 | 59.00 | 34.00 | 10.00 | 7.00 | 10.00 | 0.64 | 1.43 |
| 4 | 476.00 | 122.00 | 25.00 | 35.00 | 38.00 | 0.40 | 0.71 |
| 5 | 5.00 | 10.00 | 2.00 | 3.00 | 4.00 | 0.63 | 0.67 |
| Mean | 128.20 | 45.60 | 10.60 | 12.00 | 13.80 | 0.55 | 0.98 |
| Stnd. Dev. | 197.98 | 45.79 | 9.29 | 13.38 | 14.25 | 0.11 | 0.31 |

Fig. 19C

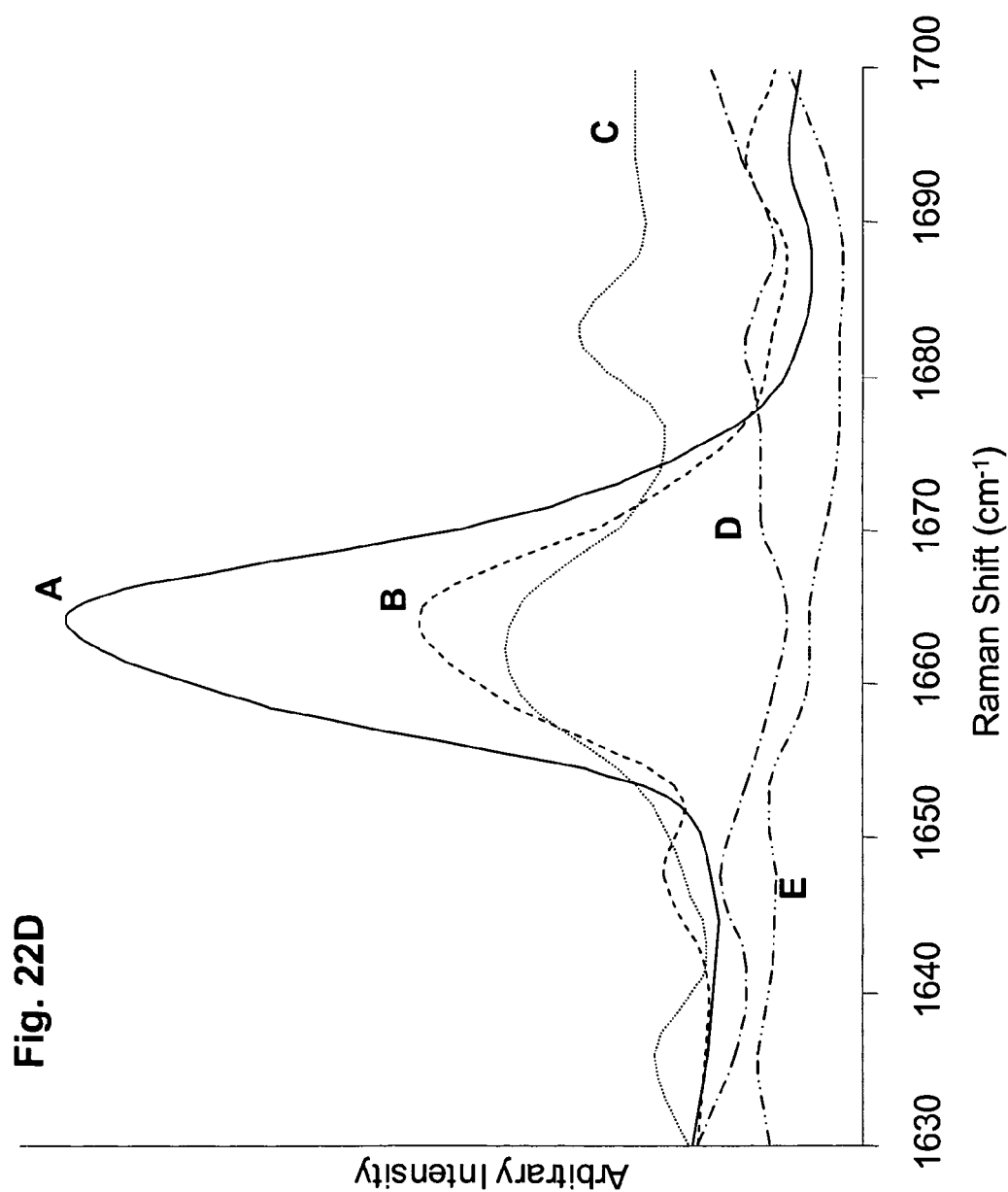

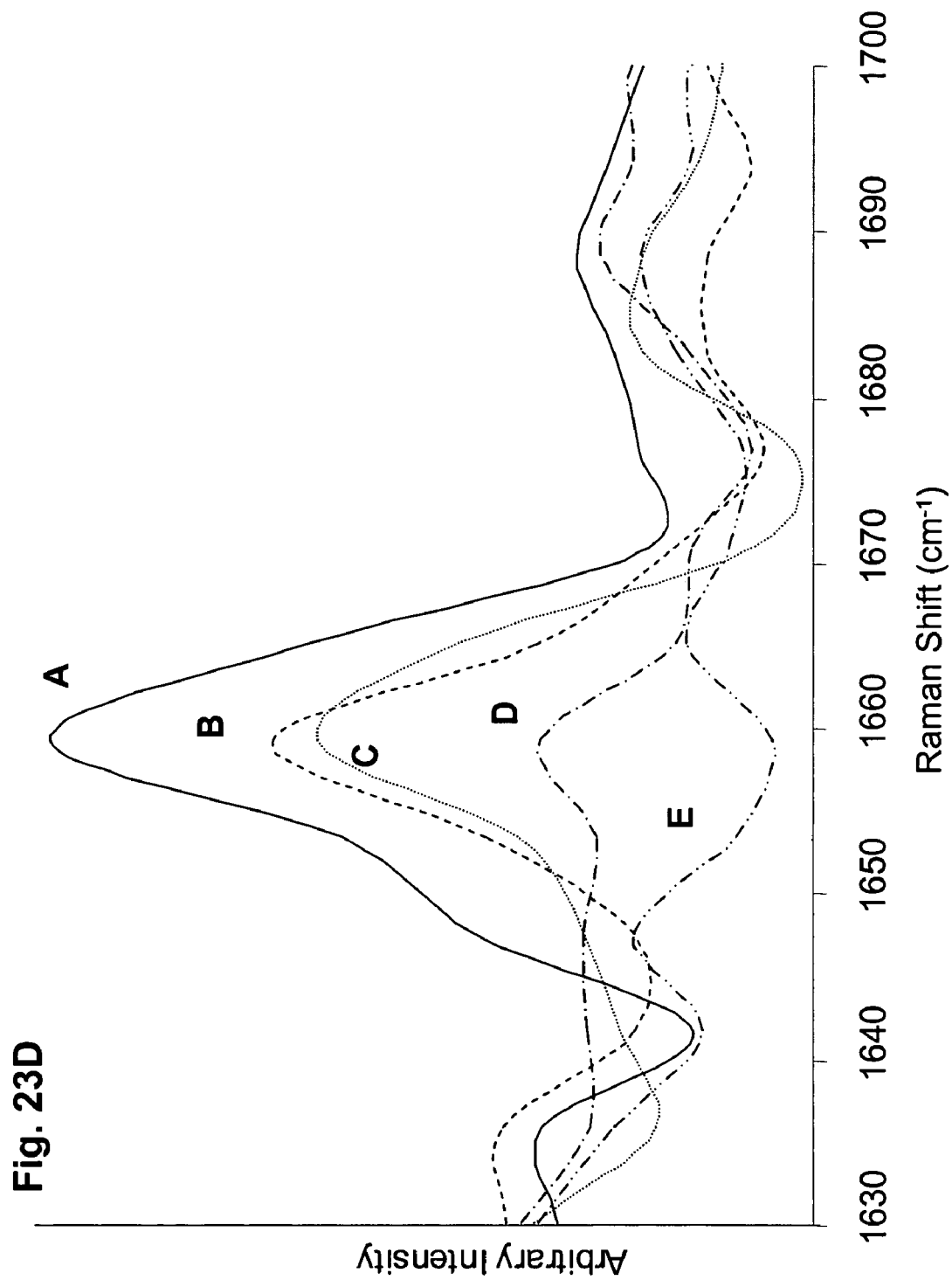

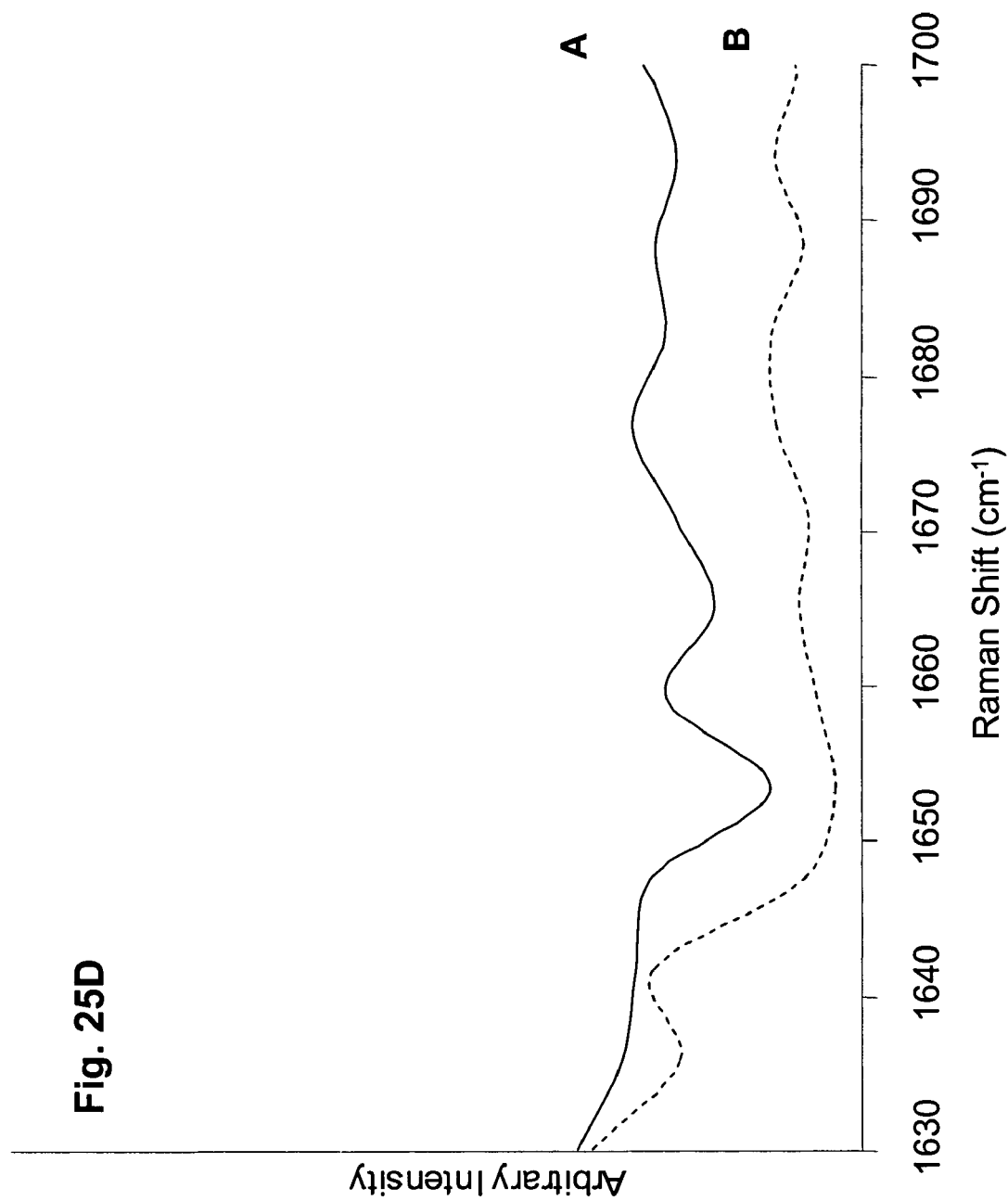

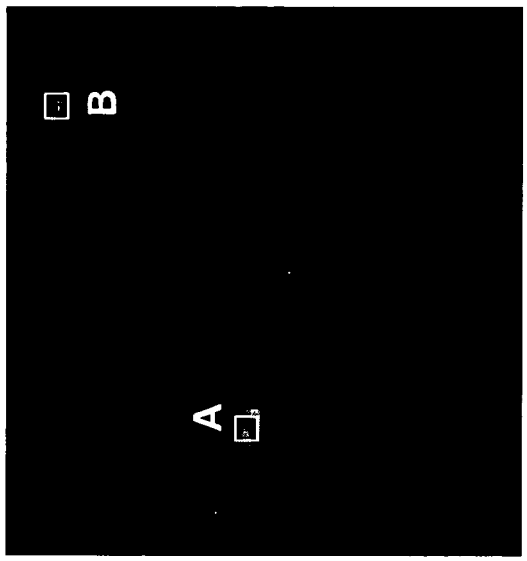
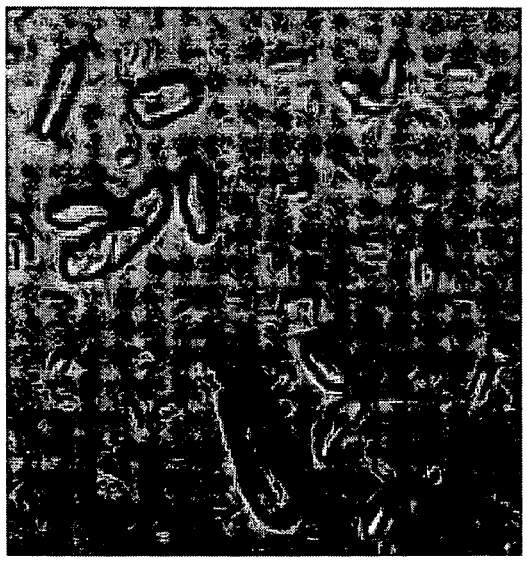
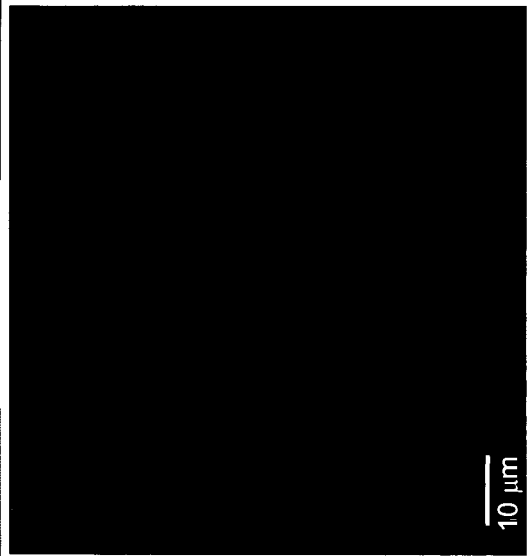
Fig. 26A
Fig. 26B
Fig. 26C

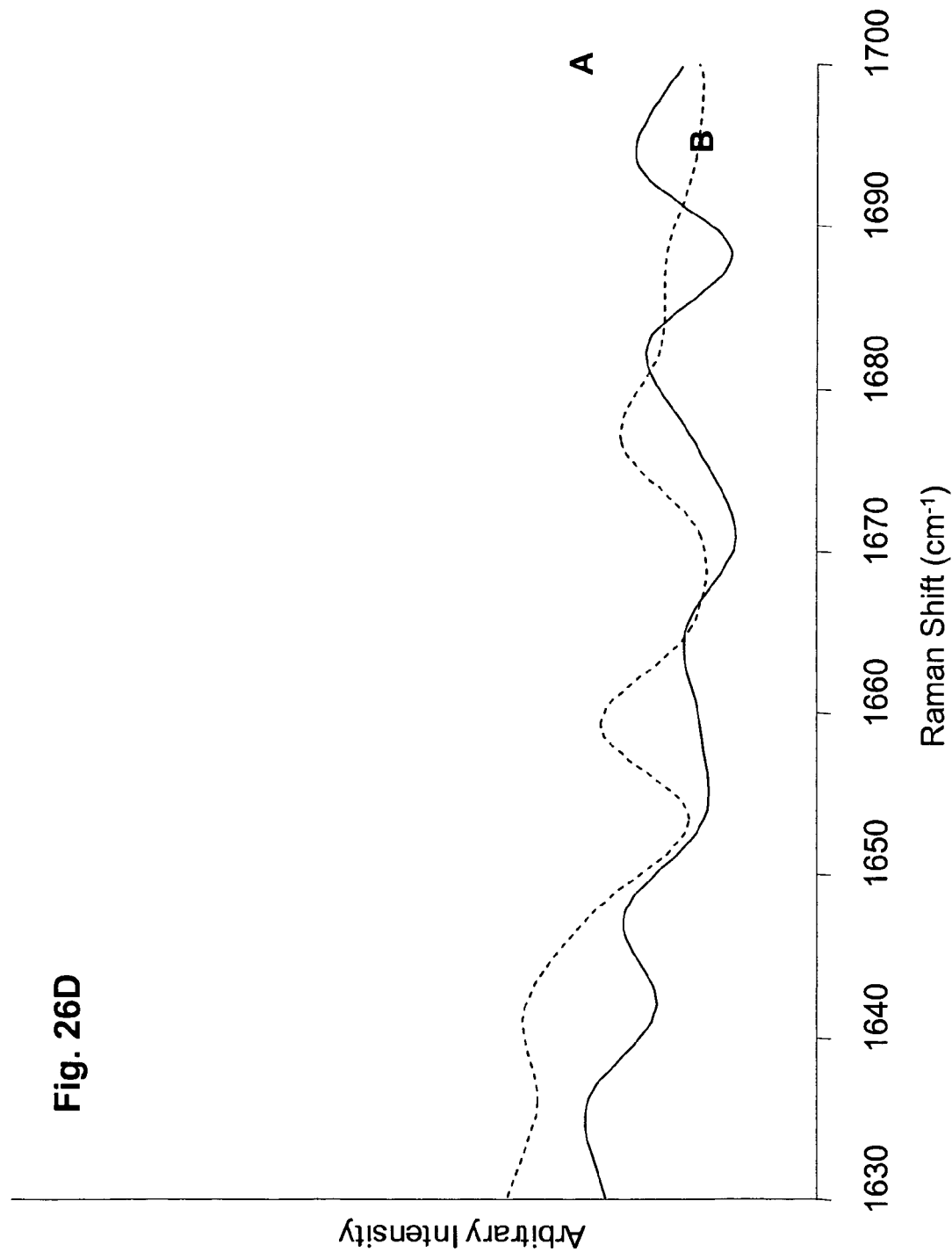

| ROI 1 | | | | | | | |
|---|---|---|---|---|---|---|---|
| Object | Area (µm²) | Perimeter (µm) | Feret 1 (µm) | Feret 2 (µm) | Max. Chord (µm) | Shape | Aspect |
| 1 | 0.61 | 3.43 | 0.62 | 1.09 | 1.09 | 0.65 | 0.57 |
| 2 | 0.54 | 3.28 | 0.78 | 0.94 | 0.94 | 0.63 | 0.83 |
| 3 | 26.68 | 36.37 | 6.40 | 7.65 | 8.43 | 0.25 | 0.84 |
| 4 | 0.19 | 2.03 | 0.62 | 0.47 | 0.62 | 0.59 | 1.33 |
| 5 | 2.46 | 10.15 | 1.72 | 2.65 | 2.97 | 0.30 | 0.65 |
| mean | 6.10 | 11.05 | 2.03 | 2.56 | 2.81 | 0.48 | 0.84 |
| stnd. dev. | 11.54 | 14.51 | 2.49 | 2.96 | 3.27 | 0.19 | 0.30 |
| ROI 2 | | | | | | | |
| Object | Area | Perimeter | Feret 1 | Feret 2 | Max. Chord | Shape | Aspect |
| 1 | 0.22 | 2.03 | 0.62 | 0.47 | 0.62 | 0.67 | 1.33 |
| 2 | 7.19 | 13.42 | 3.43 | 3.12 | 3.75 | 0.50 | 1.10 |
| 3 | 0.37 | 2.81 | 0.78 | 0.62 | 0.94 | 0.58 | 1.25 |
| 4 | 10.62 | 16.23 | 3.59 | 3.90 | 4.68 | 0.51 | 0.92 |
| mean | 4.60 | 8.62 | 2.11 | 2.03 | 2.50 | 0.56 | 1.15 |
| stnd. dev. | 5.17 | 7.26 | 1.62 | 1.74 | 2.02 | 0.08 | 0.18 |
| ROI 3 | | | | | | | |
| Object | Area | Perimeter | Feret 1 | Feret 2 | Max. Chord | Shape | Aspect |
| 1 | 0.51 | 4.06 | 0.47 | 1.56 | 1.56 | 0.39 | 0.30 |
| 2 | 0.71 | 3.90 | 1.09 | 0.94 | 1.09 | 0.58 | 1.17 |
| 3 | 0.37 | 2.81 | 0.78 | 0.62 | 0.78 | 0.58 | 1.25 |
| 4 | 0.05 | 0.94 | 0.31 | 0.16 | 0.31 | 0.70 | 2.00 |
| 5 | 1.41 | 6.40 | 1.56 | 1.40 | 1.56 | 0.43 | 1.11 |
| 6 | 0.05 | 0.94 | 0.16 | 0.31 | 0.31 | 0.70 | 0.50 |
| 7 | 1.22 | 5.93 | 1.56 | 1.25 | 1.56 | 0.44 | 1.25 |
| 8 | 1.17 | 4.68 | 1.25 | 1.09 | 1.40 | 0.67 | 1.14 |
| 9 | 5.07 | 17.01 | 2.65 | 4.06 | 4.53 | 0.22 | 0.65 |
| mean | 1.17 | 5.19 | 1.09 | 1.27 | 1.46 | 0.52 | 1.04 |
| stnd. dev. | 1.54 | 4.83 | 0.78 | 1.15 | 1.26 | 0.16 | 0.50 |
| Overall | | | | | | | |
| mean | 2.40 | 6.34 | 1.36 | 1.53 | 1.79 | 0.47 | 0.94 |
| stnd. dev. | 2.97 | 4.86 | 0.94 | 1.16 | 1.33 | 0.20 | 0.48 |

Fig. 27D

| Particle | NIST-Traceable Value | ChemImage Array Method Value: Brightfield/Raman Overlay |
|---|---|---|
| PS 1 | 0.705±0.007 | 0.71±0.01 |
| PS 2 | 5.1±0.5 | N.A.* |
| PS 3 | 2.062±0.022 | 2.1±0.01 |
| PS 4 | 10±0.59 | 10.34±0.06 |
| PS 5 | 31.1±1.7 | 30.99±1.2 |
| PS 6 | 1.031±0.012 | 1.05±0.01 |

FIG. 10 consists of FIGS. 10A and 10B. FIG. 10A depicts the chemical structure of beclomethasone dipropionate (BDP). FIG. 10B depicts a dispersive Raman spectrum of BDP generated using the same spectrometer and settings as in FIG. 4.

FIG. 11 is the overlaid Raman spectra of FIGS. 4-10, wherein the spectra are indicated with the same line styles as in FIGS. 4-10.

FIG. 12 consists of FIG. 12A, FIG. 12B and a particle size distribution (PSD) chart (FIG. 12C). FIG. 12 A depicts a polarized light micrograph of BDP. FIG. 12B is a binarized image of FIG. 12A. The PSD chart was prepared by software analysis of the binarized image of FIG. 12B.

FIG. 13 consists of FIG. 13A, FIG. 13B and a particle maximum chord length distribution graph (FIG. 13C). FIGS. 13A and 13B are replicas of FIGS. 12A and 12B. The graph was prepared by software analysis of the binarized image of FIG. 13B.

FIG. 14, consisting of FIGS. 14A, 14B, 14C, 14D, and 14E, depicts results obtained from RCI of a mixture of BDP and MCC (no water added). FIGS. 14A and 14B are brightfield reflectance and polarized light micrographs, respectively. FIG. 14C is a color Raman chemical image of the mixture, in which areas A (corresponding to BDP), B (corresponding to MCC), and C (corresponding to the background) are indicated. FIGS. 14D and 14E are Raman spectra obtained by Raman scattering analysis of regions A (solid line), B (dashed line), and C (dotted line) of FIG. 14C.

FIG. 15 consists of FIGS. 15A and 15B and a PSD data table (FIG. 15C). FIG. 15A is a grayscale Raman chemical image assessed at a Raman shift value characteristic of MCC, and FIG. 15B is a binarized image of FIG. 15A. The data in the PSD table were prepared by software analysis of the binarized image of FIG. 15B.

FIG. 16 consists of FIGS. 16A and 16B and a PSD data table (FIG. 16C). FIG. 16A is a grayscale Raman chemical image assessed at a Raman shift value characteristic of BDP, and FIG. 16B is a binarized image of FIG. 16A. The data in the PSD table were prepared by software analysis of the binarized image of FIG. 16B.

FIG. 17, consisting of FIGS. 17A, 17B, 17C, 17D, and 17E, depicts results obtained from RCI of a mixture of BDP and MCC with water added thereto. FIGS. 17A and 17B are brightfield reflectance and polarized light micrographs, respectively. FIG. 17C is a Raman chemical image of the mixture, in which areas A (corresponding to BDP), B (corresponding to MCC), and C (corresponding to the background) are indicated. FIGS. 17D and 17E are Raman spectra obtained by Raman scattering analysis of regions A (solid line), B (dashed line), and C (dotted line) of FIG. 17C.

FIG. 18 consists of FIGS. 18A and 18B and a PSD data table (FIG. 18C). FIG. 18A is a grayscale Raman chemical image assessed at a Raman shift value characteristic of MCC following addition of water, and FIG. 18B is a binarized image of FIG. 18A. The data in the PSD table were prepared by software analysis of the binarized image of FIG. 18.

FIG. 19 consists of FIGS. 19A and 19B and a PSD data table (FIG. 19C). FIG. 19A is a grayscale Raman chemical image assessed at a Raman shift value characteristic of BDP following addition of water, and FIG. 19B is a binarized image of FIG. 19A. The data in the PSD table were prepared by software analysis of the binarized image of FIG. 19B.

FIG. 20, comprising FIGS. 20A and 20B depicts a pair of polarized light micrographs of the MCC/BDP blend prior to the addition of water (FIG. 20A) and following addition of water (FIG. 20B).

FIG. 21, consisting of FIGS. 21A, 21B, 21C, 21D, and 21E, depicts results obtained from RCI of a sample of BECONASE AQ (™). FIGS. 21A and 21B depict brightfield reflectance and polarized light micrographs, respectively. FIG. 21C is a Raman chemical image of the sample assessed at a Raman shift value characteristic of BDP. FIG. 21D depicts Raman spectra assessed in several boxed regions of FIG. 21B, including region A, corresponding to BECONASE AQ (™). FIG. 21E depicts FIGS. 21A and 21C overlaid.

FIG. 22 consisting of FIGS. 22A, 22B, 22C, 22D, and 22E, depicts results obtained from RCI of a sample of BECONASE AQ (™). FIGS. 22A and 22B depict brightfield reflectance and polarized light micrographs, respectively. FIG. 22C is a Raman chemical image of the sample assessed at a Raman shift value characteristic of BDP. FIG. 22D depicts Raman spectra assessed in several boxed regions of FIG. 22B, including region A, corresponding to BECONASE AQ (™). FIG. 22E depicts FIGS. 22A and 22C overlaid.

FIG. 23, consisting of FIGS. 23A, 23B, 23C, 23D, and 23E, depicts results obtained from RCI of a sample of BECONASE AQ (™). FIGS. 23A and 23B depict brightfield reflectance and polarized light micrographs, respectively. FIG. 23C is a Raman chemical image of the sample assessed at a Raman shift value characteristic of BDP. FIG. 23D depicts Raman spectra assessed in several boxed regions of FIG. 23B, including region A, corresponding to BECONASE AQ (™). FIG. 23E depicts FIGS. 23A and 23C overlaid.

FIG. 24, consisting of FIGS. 24A, 24B, 24C, and 24D, depicts results obtained from RCI of a sample of a placebo formulated like BECONASE AQ (™), but without BDP. FIGS. 24A and 24B depict brightfield reflectance and polarized light micrographs, respectively. FIG. 24C is a Raman chemical image of the sample assessed at a Raman shift value characteristic of BDP. FIG. 24D depicts Raman spectra assessed in several boxed regions of FIG. 24B.

FIG. 25, consisting of FIGS. 25A, 25B, 25C, and 25D, depicts results obtained from RCI of a sample of a placebo formulated like BECONASE AQ (™), but without BDP. FIGS. 25A and 25B depict brightfield reflectance and polarized light micrographs, respectively. FIG. 25C is a Raman chemical image of the sample assessed at a Raman shift value characteristic of BDP. FIG. 25D depicts Raman spectra assessed in several boxed regions of FIG. 25B.

FIG. 26, consisting of FIGS. 26A, 26B, 26C, and 26D, depicts results obtained from RCI of a sample of a placebo formulated like BECONASE AQ (™), but without BDP. FIGS. 26A and 26B depict brightfield reflectance and polarized light micrographs, respectively. FIG. 26C is a Raman chemical image of the sample assessed at a Raman shift value characteristic of BDP. FIG. 26D depicts Raman spectra assessed in several boxed regions of FIG. 26B.

FIG. 27 consists of FIGS. 27A, 27B, and 27C and a PSD table (FIG. 27D). FIGS. 27A, 27B, and 27C depict binarized Raman chemical images assessed at a Raman shift characteristic of BPD at three regions of interest of the BECONASE AQ (™) nasal spray samples depicted in FIGS. 21, 22, and 23. The data in the PSD table were prepared by software analysis of the binarized image of FIGS. 27A, 27B, and 27C (ROI 1, ROI 2, and ROI 3, respectively in the PSD table), and indicated that the mean particle size was 1.79±1.33 micrometers.

FIG. 28 is a PSD graph which depicts data prepared by software analysis of the binarized image of FIGS. 27A, 27B, and 27C.

FIGS. 29 consists of FIGS. 29A, 29B, and 29C and a particle size standard table (FIG. 29D). FIG. 29A depicts a brightfield reflectance micrograph of 10 micron NIST-traceable polystyrene microspheres. FIG. 29B depicts a Raman chemical image of the microspheres, assessed at a Raman chemical shift value characteristic of polystyrene. FIG. 29C is a color image of FIGS. 29A and 29B overlaid. The data depicted in FIG. 29C were used to determine sphere sizes (maximum chord sizes, in micrometers) shown in the table. The table also lists NIST traceable values for the six size standards assessed. The spheres indicated with an asterisk in the particle size standard table did not form arrays.

DETAILED DESCRIPTION OF THE INVENTION

The invention relates to methods of assessing one or more geometric properties of a particle of a substance using a Raman spectroscopic property of the substance. The methods are useful, for example, for assessing particle sizes and size distributions in mixtures containing both particles of the substance and other materials. The methods can also be used to assess association between compounds and particles in a sample, such as agglomeration of particles of different substances and inclusion of multiple substances in a single particle.

The present invention is directed to overcoming one or more of the limitations inherent to current methods for the determination of geometric properties, such as particle size distribution (PSD), for complex mixtures like inhalable pharmaceutical products. Restrictions associated with prior art methods for determining PSDs cannot generate information for particular molecular species in complex drug formulations.

The methods described herein relate to methods of assessing geometric properties (e.g., PSD) of particles of a particular substance (e.g., a single chemical compound) in a composition. The methods are not affected by the presence of particles of other substances (e.g., pharmaceutical excipients or contaminants) in the composition. Very briefly, the methods comprises immobilizing the particles (if necessary), acquiring Raman chemical imaging data characteristic of the substance of interest, and processing that data using image processing techniques to describe a geometric property of the particles. The methods described herein have the advantage of being able to determine the identity and geometric properties of multiple particles substantially simultaneously, even if the particles are particles of one or more substances.

Definitions

As used herein, each of the following terms has the meaning associated with it in this section.

A "particle of a substance" is an entity having a phase boundary with one or more surrounding entities, wherein the entity comprises the substance. Examples of a particle of a substance include a solid phase of the substance surrounded by a liquid or gaseous phase and a first liquid phase that comprises the substance and is surrounded by a second liquid phase that substantially does not comprise the substance. A particle can consist entirely or essentially of the substance, or the particle can comprise other materials.

"Association" between and among particles refers to agglomeration, bonding, or any other close physical (including electrostatic) interaction of two or more particles, whether permanent or short-lived.

A particle is "effectively immobilized" if it is maintained in a location and an orientation that do not substantially change during the period of Raman scattering analysis described herein.

The terms "optical" and "spectroscopic" are used interchangeably herein to refer to properties of materials (and to methods of assessing such properties). The term "spectroscopic" is generally understood to refer to the interaction of electromagnetic radiation, electrons, or neutrons with the materials. The term "optical" typically refers to an interaction with electromagnetic radiation. For example, although electron microscopy is not always commonly considered a "spectroscopic" or "optical" method, the two terms are used inclusively herein to encompass electron microscopy and other methods of assessing interaction of a material with visible, ultraviolet, or infrared light, with neutrons, with electrons, or with other radiation.

"Spectral resolution" means the ability of a radiation detection system to resolve two spectral peaks.

Two images are combined "in an aligned manner" when the combined image corresponds at every point to essentially the same point in each of the two individual images. Thus, two images of a microscopic field that includes a circle, a square, and a star are combined in an aligned manner when each of the circle, square, and star of the two images of the field overlap essentially precisely in the combined image.

Detailed Description

The invention relates to a method of assessing a geometric property of a particle of a substance in a microscopic field, or to multiple particles of the same or different substances. The method comprises irradiating a particle and generating an image of Raman-shifted radiation scattered from the particle at one or more Raman shift values characteristic of the substance. The geometric property can be determined from the image. Because Raman scattering intensities and shift values are characteristic of the compound scattering the incident radiation, geometric properties of particles of differing composition can be assessed in mixtures of such particles. Furthermore, by generating a Raman chemical image of an entire field of view, geometric properties of substantially all particles in the field can be assessed substantially simultaneously.

Raman Spectroscopy

Raman spectroscopy provides information about the vibrational state of molecules. Many molecules have atomic bonds capable of existing in a number of vibrational states. Such a molecule is able to absorb incident radiation that matches a transition between two of its allowed vibrational states and to subsequently emit the radiation. Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in frequency can be more easily distinguished from the Rayleigh scattered light.

Because Raman spectroscopy is based on irradiation of a sample and detection of scattered radiation, it can be employed non-invasively and non-destructively, such that it is suitable for analysis of biological samples in situ. Thus, little or no sample preparation is required. In addition, water exhibits very little Raman scattering, and Raman spectroscopy techniques can be readily performed in aqueous environments.

The Raman spectrum of a material can reveal the molecular composition of the material, including the specific functional groups present in organic and inorganic molecules.

Raman spectroscopy is useful for detection of pharmaceutical and other chemical agents because most, if not all, of these agents exhibit characteristic 'fingerprint' Raman spectra, subject to various selection rules, by which the agent can be identified. Raman peak position, peak shape, and adherence to selection rules can be used to determine molecular identity and to determine conformational information (e.g., crystalline phase, degree of order, strain, grain size) for solid materials.

In the past several years, a number of key technologies have been introduced into wide use that have enabled scientists to largely overcome the problems inherent to Raman spectroscopy. These technologies include high efficiency solid-state lasers, efficient laser rejection filters, and silicon CCD detectors. In general, the wavelength and bandwidth of light used to illuminate the sample is not critical, so long as the other optical elements of the system operate in the same spectral range as the light source.

In order to detect Raman scattered light and to accurately determine the Raman shift of that light, the sample should be irradiated with substantially monochromatic light, such as light having a bandwidth not greater than about 1.3 nanometers, and preferably not greater than 1.0, 0.50, or 0.25 nanometer. Suitable sources include various lasers and polychromatic light source-monochromator combinations. It is recognized that the bandwidth of the irradiating light, the resolution of the wavelength resolving element(s), and the spectral range of the detector determine how well a spectral feature can be observed, detected, or distinguished from other spectral features. The combined properties of these elements (i.e., the light source, the filter, grating, or other mechanism used to distinguish Raman scattered light by wavelength) define the spectral resolution of the Raman signal detection system. The known relationships of these elements enable the skilled artisan to select appropriate components in readily calculable ways. Limitations in spectral resolution of the system (e.g., limitations relating to the bandwidth of irradiating light, grating groove density, slit width, interferometer stepping, and other factors) can limit the ability to resolve, detect, or distinguish spectral features. The skilled artisan understands that and how the separation and shape of Raman scattering signals can determine the acceptable limits of spectral resolution for the system for any of the Raman spectral features described herein.

Raman Chemical Imaging

Spectroscopic methods can be extended to chemical imaging (also known as spectroscopic imaging) techniques through the use of imaging spectrometers such as liquid crystal imaging spectrometers. The development of this technology in recent years has enabled widefield spectroscopic imaging to develop and mature. Chemical imaging is a versatile technique that is well suited for analysis of complex heterogeneous materials. Applications of chemical imaging range from the analysis of polymer blends, defect status analysis in semiconductor materials, inclusions in human breast tissue, characterization of corrosion samples and detection, classification and identification of biological and chemical warfare agents. Chemical imaging provides a potential solution for obtaining both qualitative and quantitative image information about molecular composition and morphology materials allowing a more accurate and more rapid analysis than traditional imaging or 'wet' chemical methods.

Raman chemical imaging (RCI) combines Raman spectroscopy with digital imaging for molecular-specific analysis of materials. This technology allows images of samples to be constructed by recording Raman scattered light at discrete wavelengths emanating from defined locations in an illuminated sample. A spectrum is generated corresponding to millions of spatial locations at the sample surface by tuning the liquid crystal imaging Raman spectrometer over a range of wavelengths and collecting images intermittently. Depending on the materials, depth-related information can also be obtained by using different excitation wavelengths or by capturing Raman chemical images at incremental planes of focus. Contrast is generated in the images based on the relative amounts of Raman scatter that is generated by the different species located throughout the sample. Since a Raman spectrum is generated for each pixel location, univariate and/or multivariate (i.e., chemometric) analysis tools such as correlation analysis, Principal Component Analysis (PCA), and factor rotation, including Multivariate Curve Resolution (MCR), can be applied to the image data to extract pertinent information.

A spatial resolving power of approximately 250 nanometers has been demonstrated for Raman chemical imaging using laser illumination at visible wavelengths. This is almost two orders of magnitude better than infrared imaging that is typically limited to a spatial resolution of about 20 microns, owing to diffraction. In addition, image definition (based on the total number of imaging pixels) can be very high for RCI based on liquid crystal optics because high pixel density detectors (often 1 million or more detector elements per detector) can be used. The wavelength of light used for illumination is not critical and can be in the range from 220 to 1100 nanometer.

An apparatus for Raman chemical imaging has been described by Treado in U.S. Pat. No. 6,002,476, and in U.S. patent application Ser. No. 09/619,371, filed 19 Jul. 2000, which are incorporated herein by reference. Other descriptions of Raman chemical imaging are U.S. patent application Ser. No. 09/800,953, filed 7 Mar. 2001; U.S. patent application Ser. No. 09/976,391, filed 21 Oct. 2001; U.S. patent application Ser. No. 10/185,090, filed 27 Jun. 2002; U.S. patent application Ser. No. 10/184,580 filed 27 Jun. 2002; U.S. provisional patent application 60/144,518, filed 19 Jul. 1999; U.S. provisional patent application 60/347,806, filed 10 Jan. 2002; U.S. provisional patent application 60/144,518, filed 19 Jul. 1999; U.S. provisional patent application 60/187,560, filed 28 Mar. 2000; U.S. provisional patent application 60/239,969, filed 13 Nov. 2000; U.S. provisional patent application 60/301,708 filed, 28 Jun. 2001; and U.S. provisional patent application 60/422,604, filed 21 Nov. 2002. Each of the foregoing patents and applications is incorporated herein by reference.

RCI instrument configurations can include platforms based on a RCI microscope, for example. An example of a commercially available device which is suitable for use in the methods described herein is a laboratory or transportable field Raman microscope such as the FALCON Raman microscope (™; ChemImage Corporation, Pittsburgh, Pa.).

RCI Microscope-Based System

An RCI microscope such as the FALCON (™) system described above combines in a single platform a solid state laser for sample excitation, a refractive optical microscope base, which is equipped with infinity-corrected microscope objectives, an automated XYZ translational microscope stage, and a quartz tungsten halogen (QTH) lamp and/or a mercury (Hg) lamp. Also a part of the microscope system is an analog color charge-coupled device (CCD) detector for ordinary optical image collection and digital image collection, a liquid crystal imaging spectrometer for spectroscopic image wavelength selection, a thermoelectrically cooled (TE) Si CCD detector for Raman chemical image capture, and a remote, dispersive monochromator equipped with a CCD detector for dispersive spectral collection.

Ordinary optical imagery of the sample can be obtained using a mirror, beamsplitter, or prism arrangement inserted into the turret wheel of the microscope by collecting an image with an analog or digital color or monochrome charge-coupled device (CCD) or CMOS detector. In spectroscopic imaging mode, the magnified spectroscopic image is coupled through a liquid crystal imaging spectrometer and collected on a Si CCD detector for RCI. A central processing unit, typically a Pentium computer, is used for spectroscopic image collection and processing. The analog color CCD, Si CCD, automated XYZ translational microscope stage (controlled by way of a controller), and liquid crystal imaging spectrometer (controlled by way of a liquid crystal imaging spectrometer controller) are operated with commercial software, such as the CHEMAQUIRE (™; ChemImage Corporation, Pittsburgh, Pa.) or CHEMIMAGE XPERT (™; ChemImage Corporation, Pittsburgh, Pa.) software packages, either alone or in conjunction with the CHEMANALYZE (™; ChemImage Corporation, Pittsburgh, Pa.) software package.

By introducing a polarization sensitive beam splitting element in the optical path prior to the liquid crystal imaging spectrometer, a portion of the signal from the sample may be coupled to a remote dispersive spectrometer. This allows conventional spectroscopic tools to be used to gather spectra for traditional, high-speed spectral analysis. The spectrometers can be any of a fixed filter spectrometer, a grating-based spectrometer, a Fourier transform spectrometer, and an acousto-optic spectrometer, for example.

Preferably, liquid crystal (LC) imaging spectrometer technology is used for wavelength selection. The LC imaging spectrometer can, for example, be one of a Lyot liquid crystal tunable filter (LCTF), an Evans Split-Element LCTF, a Solc LCTF, a ferroelectric LCTF, a liquid crystal Fabry Perot (LCFP), a hybrid filter that combines two or more of the above-mentioned LC filter types, and one of the above mentioned filter types in combination with fixed bandpass and bandreject filters, which can be of the dielectric, rugate, holographic, color absorption, acousto-optic or polarization filter types.

The RCI microscope can be used as a volumetric imaging instrument by moving the sample through focus in the Z-axial dimension, collecting images in and out of focus, and reconstructing a volumetric image of the sample in software. For samples having some volume (bulk materials, surfaces, interfaces, interphases), volumetric chemical imaging has been shown to be useful for failure analysis, product development, and routine quality monitoring. The potential also exists for performing quantitative analysis simultaneous with volumetric analysis. Volumetric imaging can be performed in a non-contact mode without modifying the sample through the use of numerical confocal techniques, which require that the sample be imaged at discrete focal planes. The resulting images are processed and reconstructed and visualized. Computational optical sectioning reconstruction techniques based on a variety of strategies have been demonstrated, including nearest neighbors and iterative deconvolution.

Particle Analysis Method

Analysis of particles of a composition identifiable by Raman scattering analysis is performed by collecting RCI data from sample particles, such as substantially immobilized sample particles. From the RCI data, a Raman chemical image is generated at one or more Raman shift values characteristic of the component of interest to yield a two- or three-dimensional image of the spatial distribution of the component. The image is subjected to any of a variety of known univariate and/or multivariate image processing techniques that are known in the art in order to determine at least one geometric property of the component particles. Such geometric properties can be used to describe the properties of the component particles in the sample.

If desired, an optical or spectroscopic image of the field of view is made at substantially the same time as the RCI data are collected (or at least near enough in time that the particles in the field have not substantially moved). A dispersive Raman image of the entire field can also be collected. Because the geometric property(ies) are calculated from RCI data at a Raman shift value (i.e., wavenumber) characteristic of the substance of interest (or at two or more such characteristic values), the presence of other substances or particles in the sample does not affect assessment of the particles of interest, at least so long as the other substance(s) or particle(s) do not scatter radiation with the same intensity at every Raman shift value. An optical or spectroscopic image of the field can indicate the presence, extent, and geometric properties of particles of components other than the substance of interest in the composition that is analyzed.

The present methods have the advantage, relative to prior optical microscopy methods, that spectral information that can unambiguously identify the composition of particles can be collected simultaneously with optical information relating to particle size and shape. Furthermore, because the Raman spectral methods described herein can be used to collect spectral information characteristic of multiple compounds, prior optically-based methods of assessing particle geometry can be applied on a compound-by-compound basis to a sample containing a mixture of compounds. The Raman spectral methods described herein can distinguish a particle of a first pure substance from a particle of a second pure substance, and can also distinguish these particles from particles of mixed composition. The methods can also be used to map the relative amounts of multi-component particles in different regions of a single particle (e.g., a particle formed by agglomeration of multiple particles of differing composition).

Sample Immobilization

In one embodiment, the present invention requires effective immobilization of the substance of interest on a substrate having properties conducive to Raman chemical imaging. Such a substrate should preferably be flat, resistant to damage or modification upon laser illumination, resistant to thermal expansion, relatively Raman inactive (i.e., does not exhibit Raman scattering of the radiation with which it is illuminated), and non-interferent with the Raman light scattered from the sample.

An appropriate choice of substrate is an aluminum-coated glass microscope slide. Ordinary glass microscope slides can also be used, at least with certain laser illumination wavelengths that are apparent to skilled artisans and/or readily empirically determined. Powdered or aerosolized particles or particles suspended in a liquid can be applied to surface of such a slide and any liquid in the composition can be allowed to dry. Alternatively, compositions in which the particles of interest are suspended in a fluid can be frozen on the surface of a slide (e.g., by cooling the slide and spraying an aerosolized particle suspension thereon). As another alternative, a composition comprising particles of interest can be suspended in a polymer resin that is thereafter cured to immobilize the particles. The resin can be cured in place or sliced after curing.

If a liquid preparation of particles (e.g., solid particles suspended in liquid or a particulate liquid phase suspended in a continuous liquid phase) is to be analyzed, the preparation can be immobilized by maintaining a thin layer of the liquid under conditions (e.g., high humidity for aqueous preparations) in which the liquid will not evaporate. Alternatively, liquid samples can be sandwiched between transparent glass or plastic slides, optionally having a spacer interposed between the slides to yield a liquid layer of defined thickness.

Raman chemical imaging can also be performed on non-immobilized particles. With non-immobilized particles, it is important to take into account the time required for Raman data analysis and to limit the period of data acquisition to a period in which movement of the particles is either minimal or recorded. In instances in which Raman scattering data can be rapidly collected (e.g., when Raman scattered light is collected at one or a small number of RS values), particle motion can be disregarded. In such instances, serial collection of Raman scattering data sets can be used to assess dynamic changes (e.g., agglomeration, evaporation, precipitation, or adhesion) in a sample of particles. In instances in which a greater amount of Raman spectral data is to be collected and particle movement may be significant during the period of Raman spectral data collection, one or more techniques for correlating the location of moving particles with Raman spectral data collection must be used (e.g., optical sighting methods). Such methods are known in the art.

RCI Data Collection

RCI data can be collected using known methods. For example, a commercially available FALCON RCI microscope (™; ChemImage Corporation, Pittsburgh, Pa.) can be used according to the manufacturer's instructions.

In order to ensure proper peak positions in dispersive Raman and RCI data, the RCI instrument should be calibrated using a NIST-accepted calibration standard for Raman spectrometers. A common standard is acetaminophen. If the identity(ies) of components of the sample other than the substance of interest are known, then Raman spectral data for each of those components can be generated. This information permits identification of appropriate portions of the Raman spectrum to scan during RCI data acquisition to avoid overlapping Raman scattering peaks.

Typically, a Raman peak that both is distinctive of the substance of interest and exhibits an acceptable signal-to-noise ratio will be selected. Multiple Raman shift values characteristic of the substance can be assessed, as can the shape of a Raman spectral region that may include multiple Raman peaks. If the sample includes unknown components, then the entire Raman spectrum can be scanned during RCI data acquisition, so that the contributions of any contaminants to the data can be assessed.

In order to collect RCI data, substantially immobilized particles are brought into focus under the microscope and the appropriate data collection parameters for the instrument are set. Raman chemical image(s) are collected. Brightfield and other supporting optical imagery can also be acquired at this time to provide complimentary spatial/birefringence information in addition to the RCI data.

Data Processing

Acquired RCI optical images are subjected to one or more univariate and/or multivariate image processing strategies. Many image processing strategies are described in the art, and selection of one or more such strategies is within the level of ordinary skill in this field. Various software packages are also commercially available which are able to translate two- and three-dimensional RCI data sets geometric properties for particles. An example of suitable software for use with the FALCON (™) RCI microscope system is the CHEMIMAGE XPERT (™) software package available from ChemImage Corporation (Pittsburgh, Pa.).

A useful method for creating an easily-manipulated image which can be used for geometric property determination is creation from RCI data of one or more binary image frames, each corresponding to a particular Raman shift value and/or a particular plane of focus. For example, software can be used to assign a value of "1" to pixels that contain spatial/spectral information characteristic of the substance of interest and a value of "0" to pixels containing spatial/spectral information not characteristic of the substance. Once Raman images have been binarized, appropriate particle sizing software is applied to the processed data to determine molecule-specific particle sizes.

Typical geometrical parameters that are used to describe particle size based on two-dimensional data include the following: Area (cross-sectional area of particle); Perimeter (boundary length of particle); Feret diameter 1 (horizontal distance across particle); Feret diameter 2 (vertical distance across particle—i.e., Feret diameter along axis perpendicular to Feret diameter 1); Max chord length (maximum distance across particle); Shape factor (i.e., the value of the formula (4×pi×Area)/Perimeter ^2); Aspect ratio (Feret diameter 1/Feret diameter 2).

Typical geometrical parameters that are used to describe particle size based on three-dimensional data include the following: Volume (volume of the particle); Surface area (surface of the particle); Feret diameters (three, orthogonal to one another); Maximum chord length (maximum distance across particle); various shape factors, and various measures of aspect ratios or sphericity of the particle.

These geometrical parameters can be determined using the methods described herein or calculated from geometrical parameters that can be determined using such methods.

The dimensional limits of the particle analysis methods described herein are defined by the RCI or other spectroscopic imaging system being used. Currently, the minimum spatial differentiation limit of the ChemImage FALCON (™) RCI microscope is believed to be about 200-250 nanometers, meaning that geometrical properties of particles smaller than this could not be effectively assessed using that system. The theoretical lower limit to the size of particles that can be assessed using these methods is on the order of the diffraction limit of the incident light (taking into account known deconvolution techniques, which may lower the limit further). The methods described herein can be readily applied to any new instrument having a lower spatial differentiation limit than the FALCON (™) device.

Multiple Particle Analyses

If the composition being analyzed comprises particles having distinguishable Raman spectral properties, then the particle analytical methods described herein can be used to assess geometric properties of all of the spectrally-distinguishable types of particles in the composition. By way of example, if an aerosolized pharmaceutical composition contains two particle types that can be differentiated by their Raman scattering peaks, then RCI data can be collected at two or more Raman shift values—one Raman shift value characteristic of one particle type, and another Raman shift value characteristic of the other particle type. The two particle types can be differentiated by assessing multiple Raman scattering properties (e.g., scattering at multiple RS values) characteristic of each of the particles. This RCI data set will include information sufficient to describe geometric properties of both particle types.

Other spectral properties can be used to describe geometric properties of particles that cannot be identified by a characteristic Raman shift value. By way of example, if the composition described in the previous paragraph also contains a third particle type which can be differentiated from all other components of the composition by a characteristic fluorescent peak, then geometric properties of that third particle type can be assessed by analysis of fluorescent imaging data obtained for the characteristically-fluorescing particle. Other spectroscopic properties of a material (e.g., absorbance of visible, infrared, or near-infrared light; reflectance or polarization properties; shape or texture deduced from a microscopy technique such as scanning electron microscopy; or elemental content, such as assessed using energy dispersive spectroscopy) can also be used to identify the third particle type.

If all particle types except one in a composition can be characterized by a Raman shift value or other spectroscopic characteristic, then all particles that do not exhibit that Raman shift and/or other spectroscopic characteristic can be presumed to be the remaining particle type, and optical microscopy data can be used in combination with RCI and other spectroscopic imaging data to assess one or more geometric properties of the remaining particle type. In some instances, the chemical identity of particles other than those of a particular compound is not important and need not be determined, other than to confirm the absence of the particular compound in those particles.

EXAMPLES

The invention is now described with reference to the following Examples. These Examples are provided for the purpose of illustration only, and the invention is not limited to these Examples, but rather encompasses all variations which are evident as a result of the teaching provided herein.

Example 1

RCI Assessment of Nasal Spray Preparation

In this example, a nasal spray preparation was used which contained beclomethasone dipropionate (BDP) as an active pharmaceutical agent and the following components as inactive agents: microcrystalline cellulose (MCC); carboxymethylcellulose sodium (CMC); dextrose; benzalkonium chloride; POLYSORBATE 80 (™); and phenylethyl alcohol.

FIGS. 1 and 2 depict Raman spectra obtained using two batches (designated 1E1 and 3E1) of the nasal spray preparation. The Raman spectra shown in FIG. 1 were obtained after applying the batches to individual slides and assessing the spectra while the preparation remained wet. The spectra in FIG. 2 were obtained after applying the same batches to individual slides and assessing the spectra after the preparation had dried. The improved peak sharpness discernable in the spectra of FIG. 2 is believed to be attributable, at least in part, to the greater immobilization of the components of the dried preparations.

FIGS. 4 through 11 depict Raman spectra obtained for each component of the nasal spray preparation, assessed as individual pure components. In FIG. 11, the Raman spectra of the pure components are overlaid to show that each component has at least one Raman spectral property by which it can be distinguished from the other components of the sample.

Figure 1:
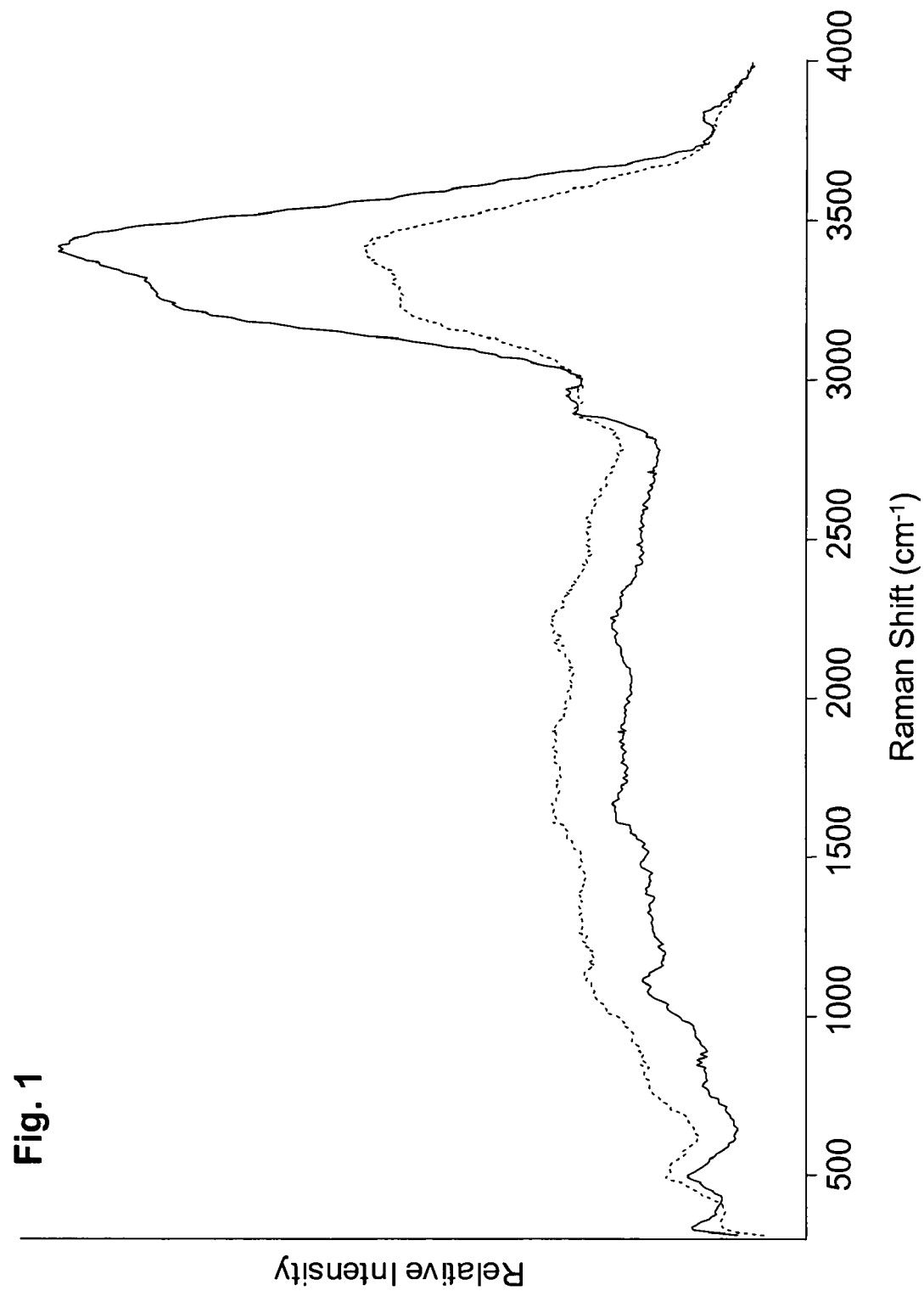
Figure 2:
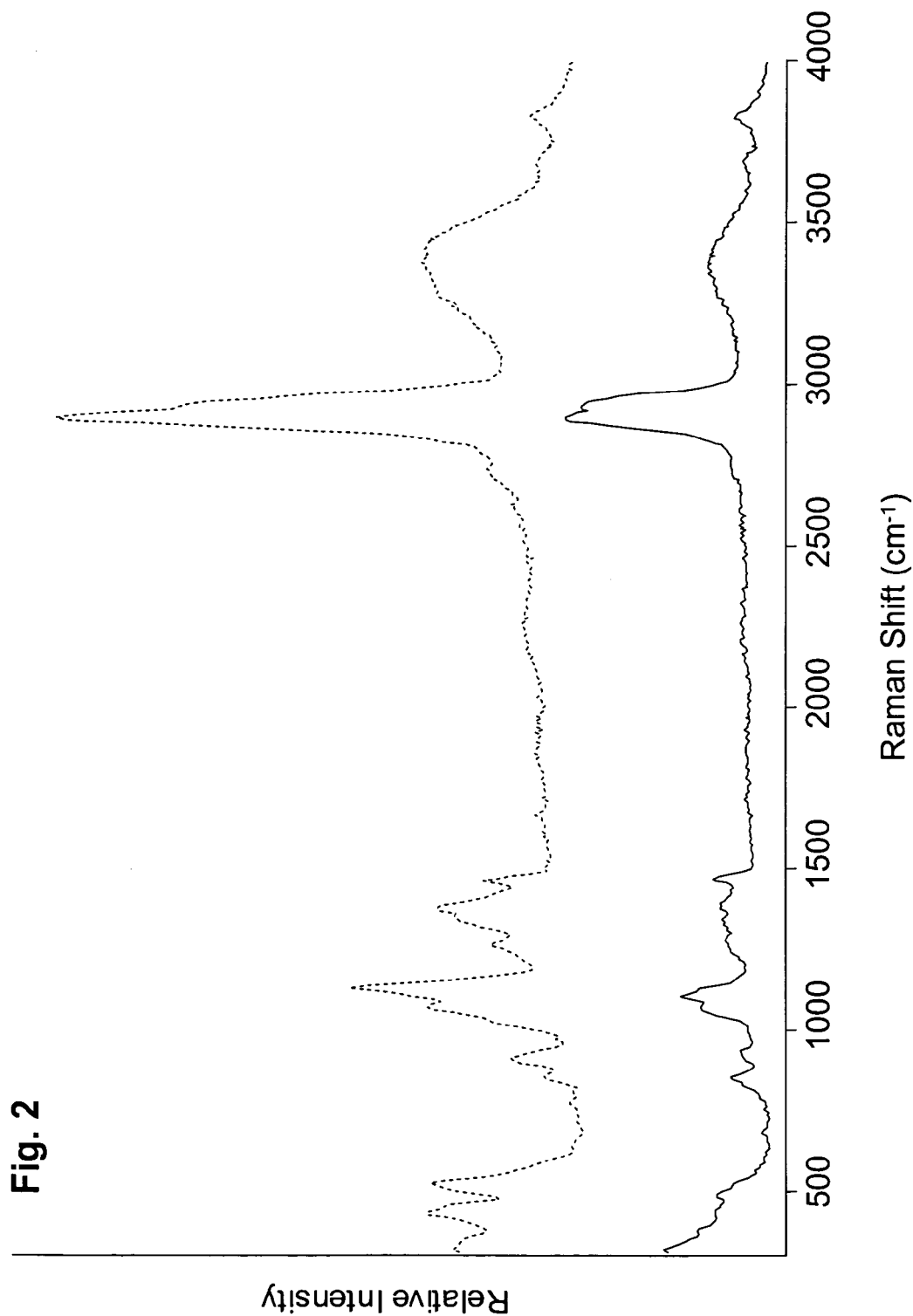
Figure 3B:
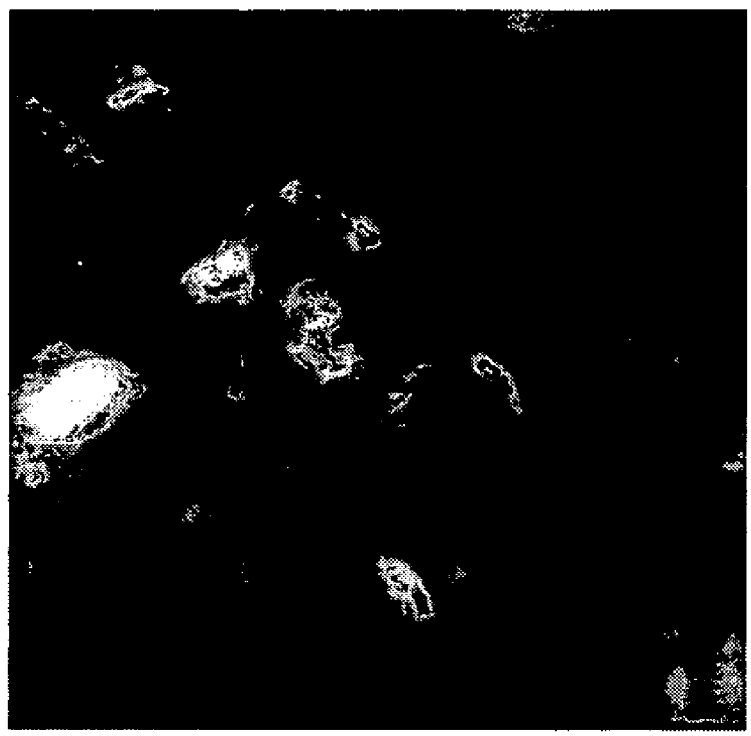
FIG. 3 depicts brightfield and polarized light micrographs (FIGS. 3A and 3B, respectively) and a Raman chemical image (FIG. 3C) of the dried batch 1E1 on a slide. The Raman spectra of regions A, B, and C of FIG. 3C are shown in FIG. 3D and indicate that components of the preparation can be distinguished by their Raman spectral properties.
Figure 3A:
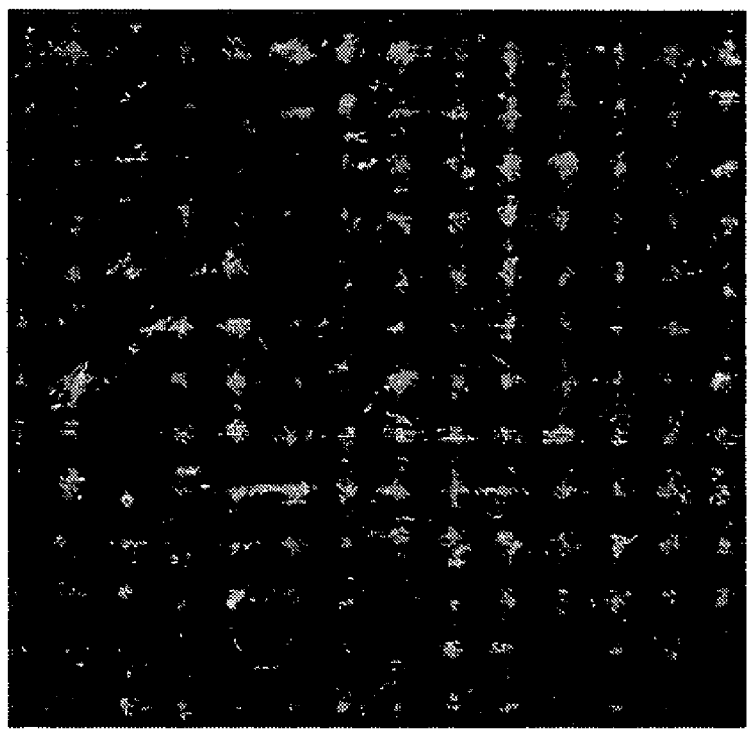
Figure 3C:
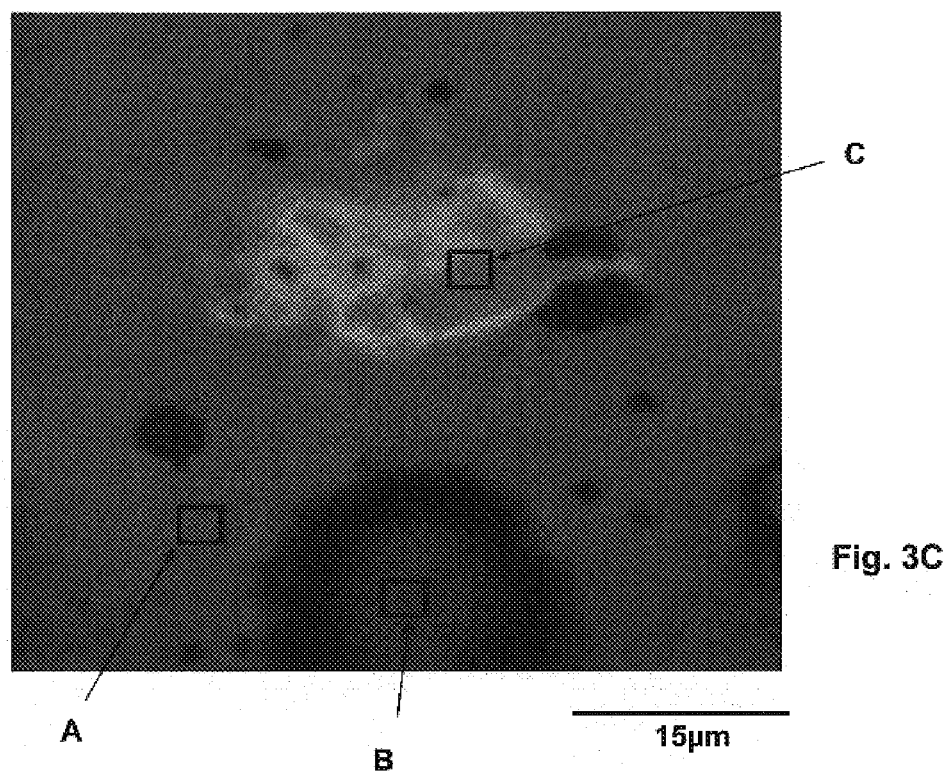
Figure 3D:
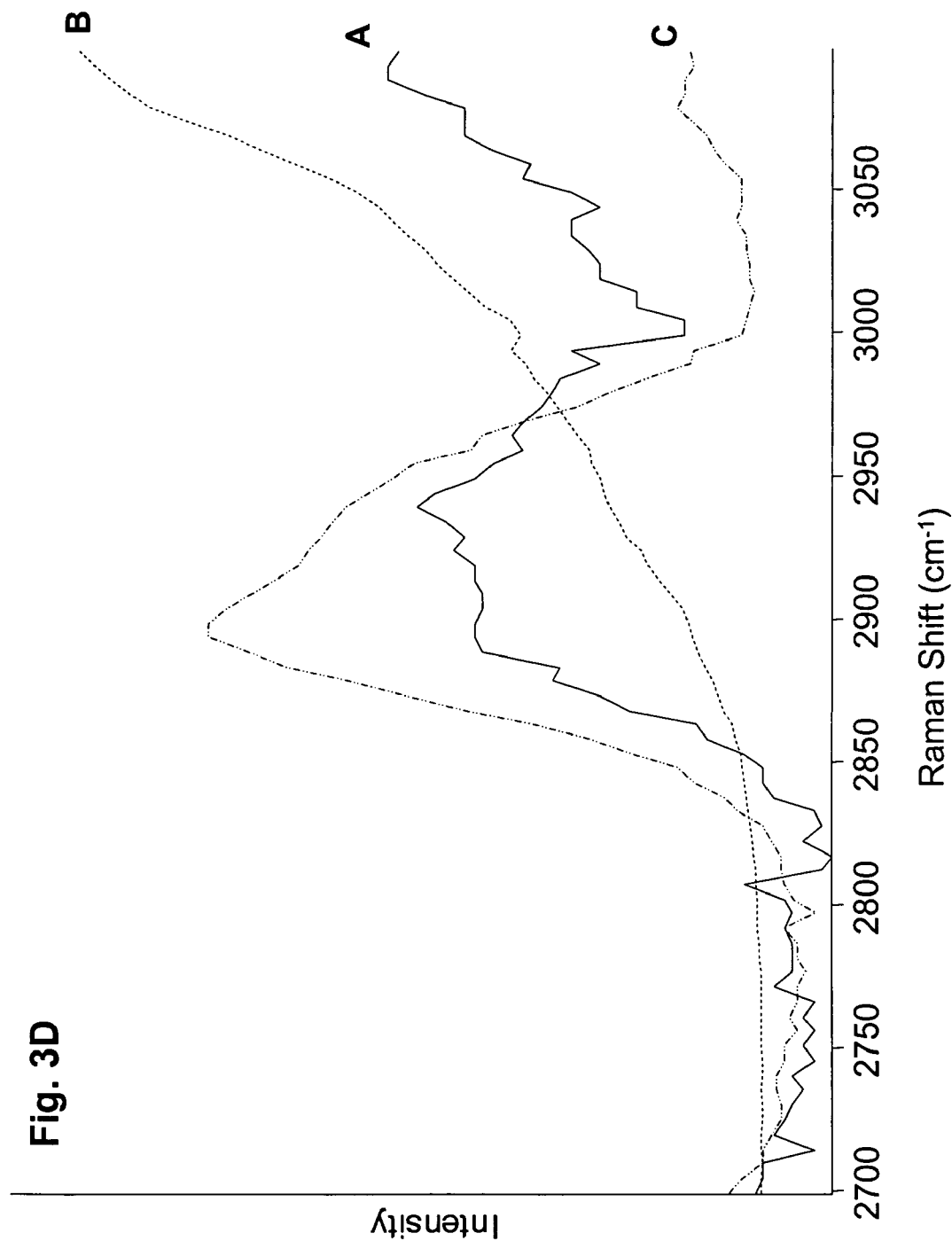
Figure 4:
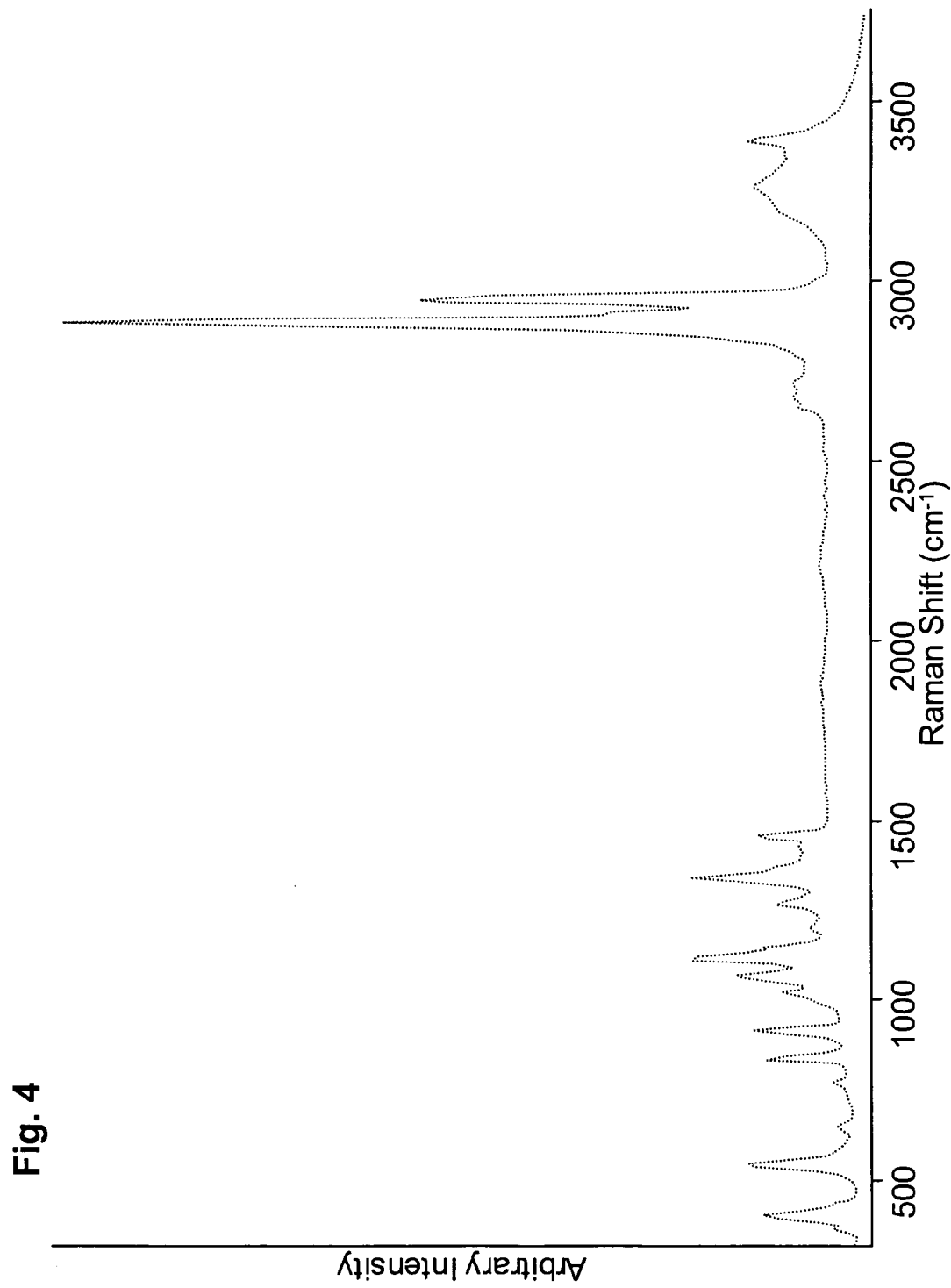
Figure 5:
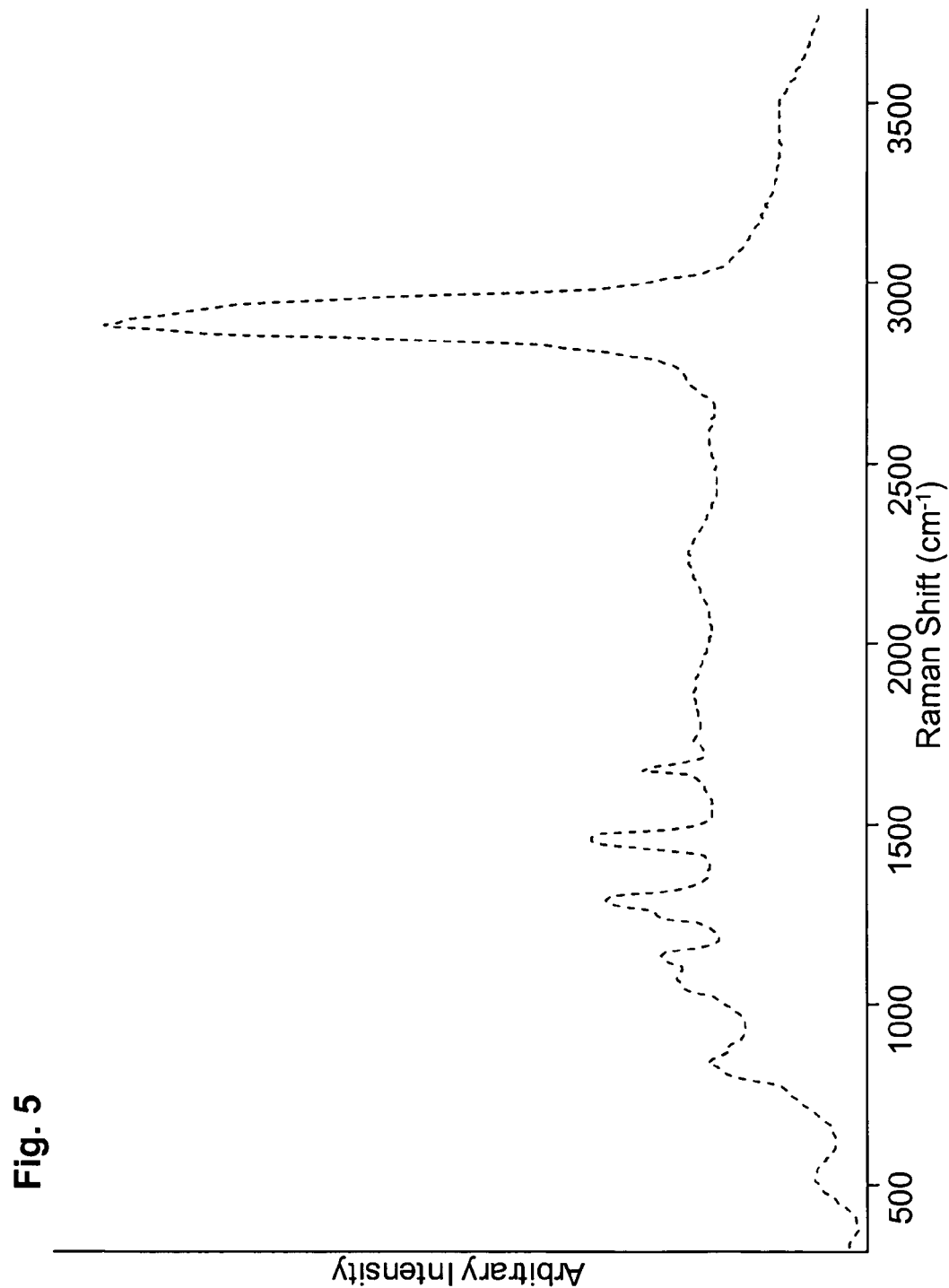
Figure 6:
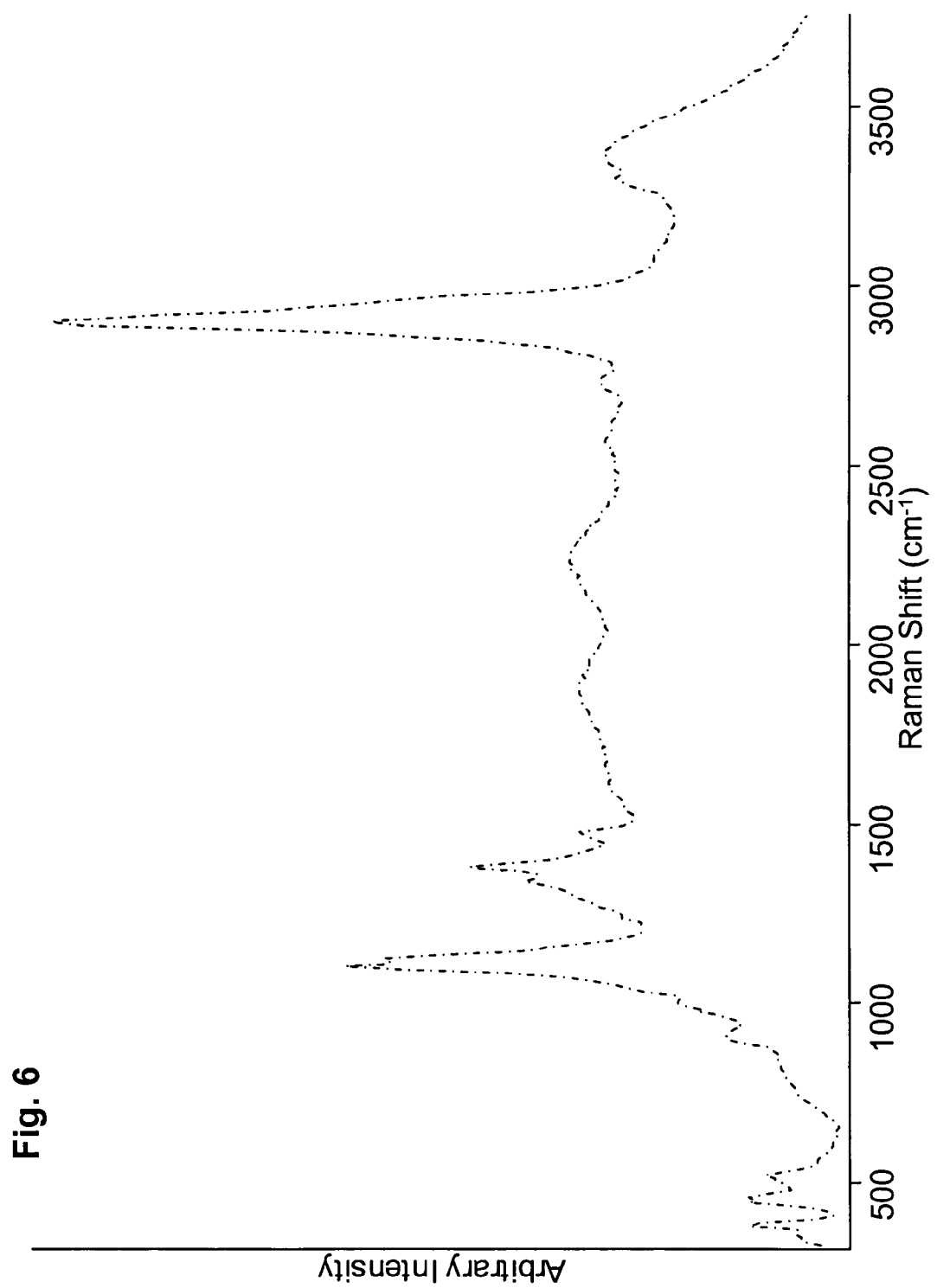
Figure 7:
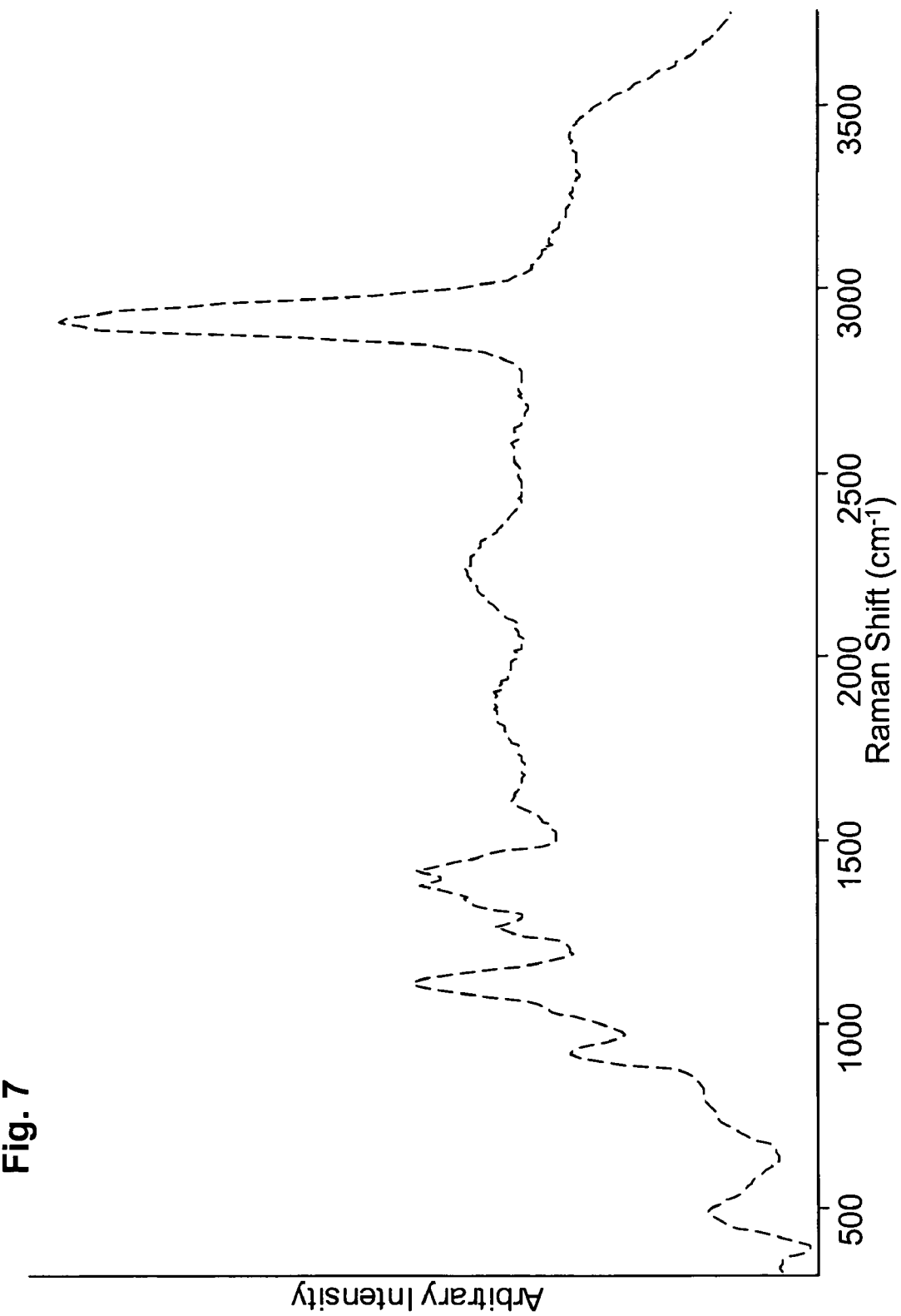
Figure 8:
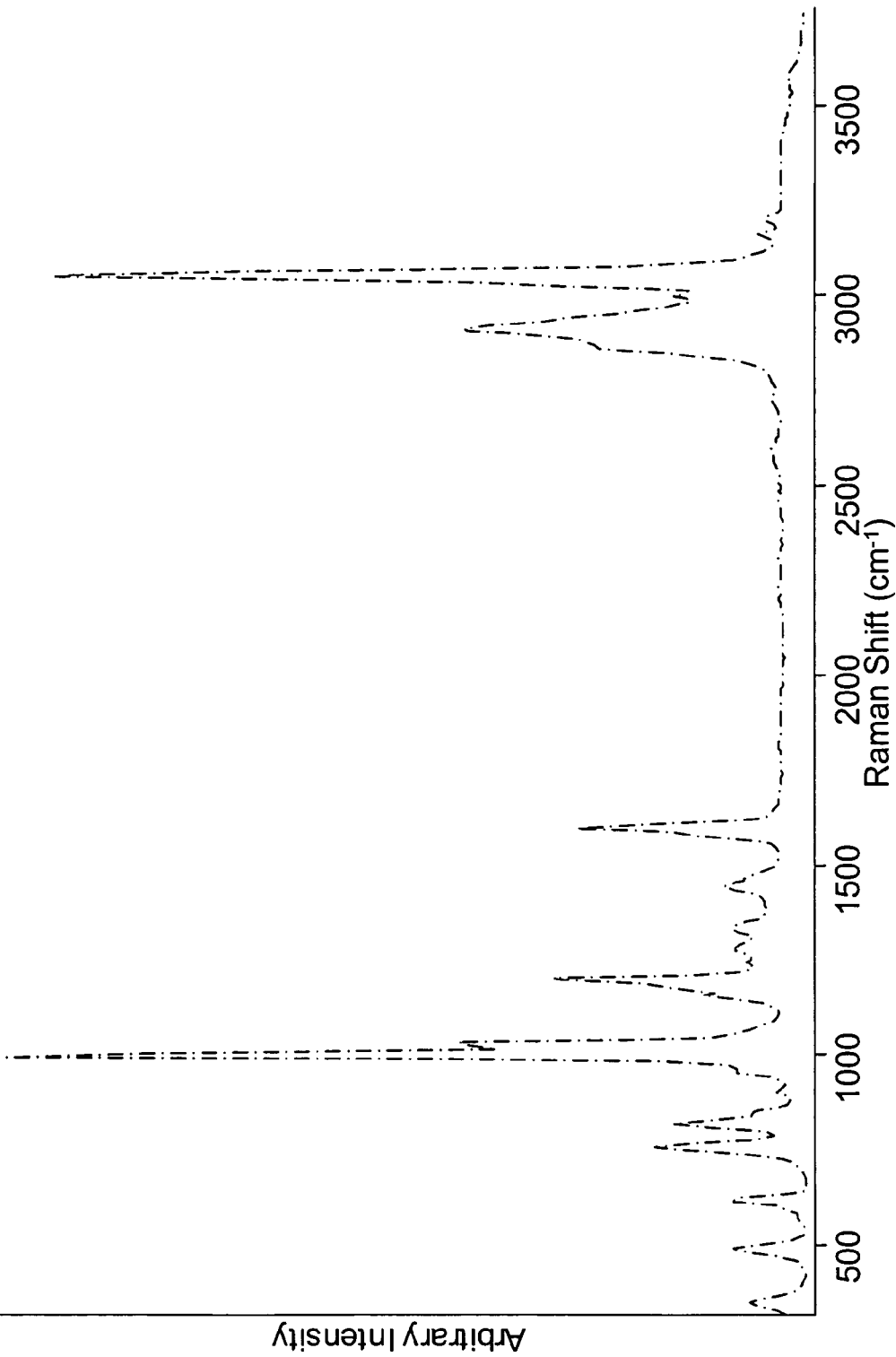
Figure 9:
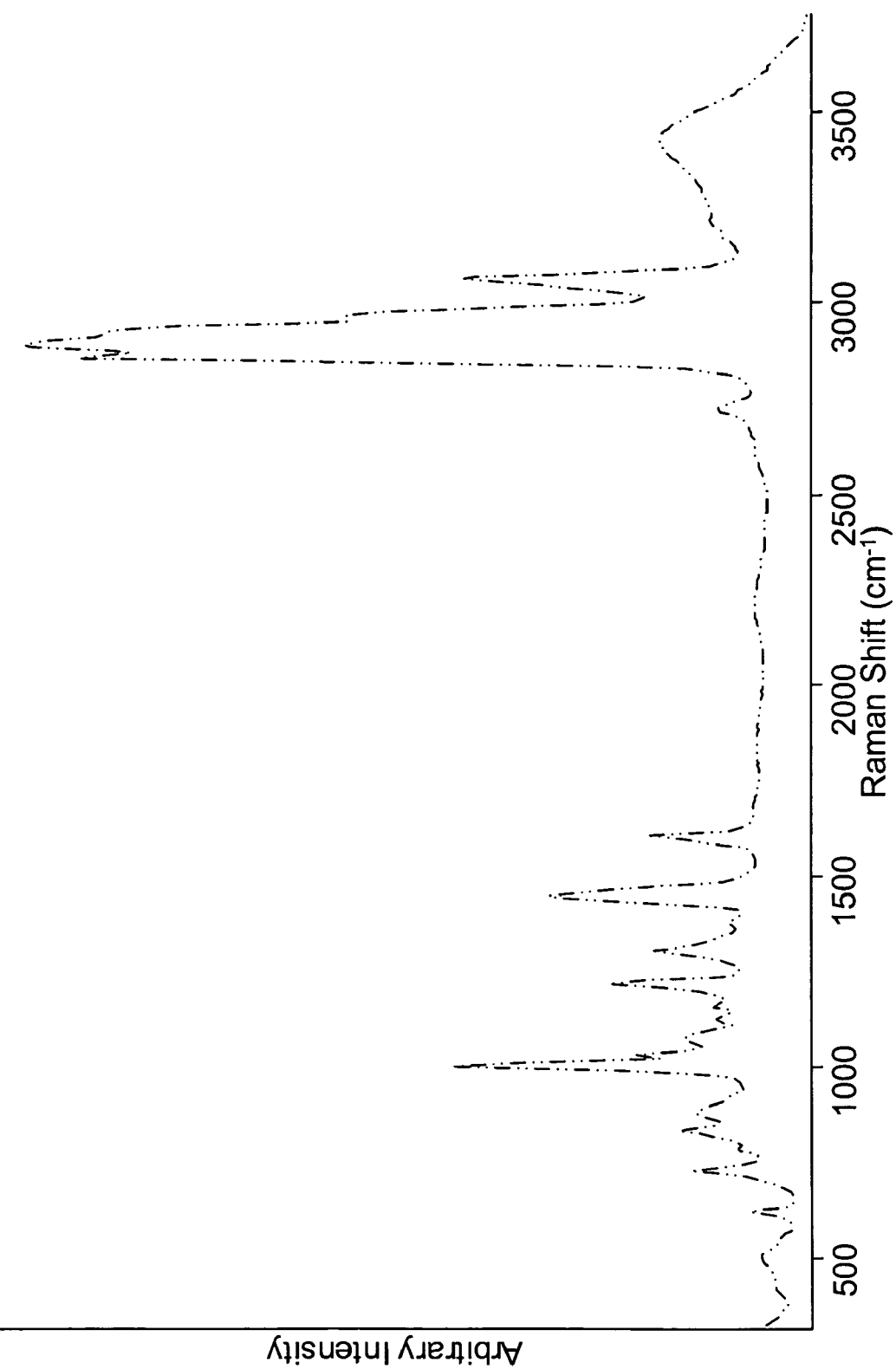
Figure 10A:
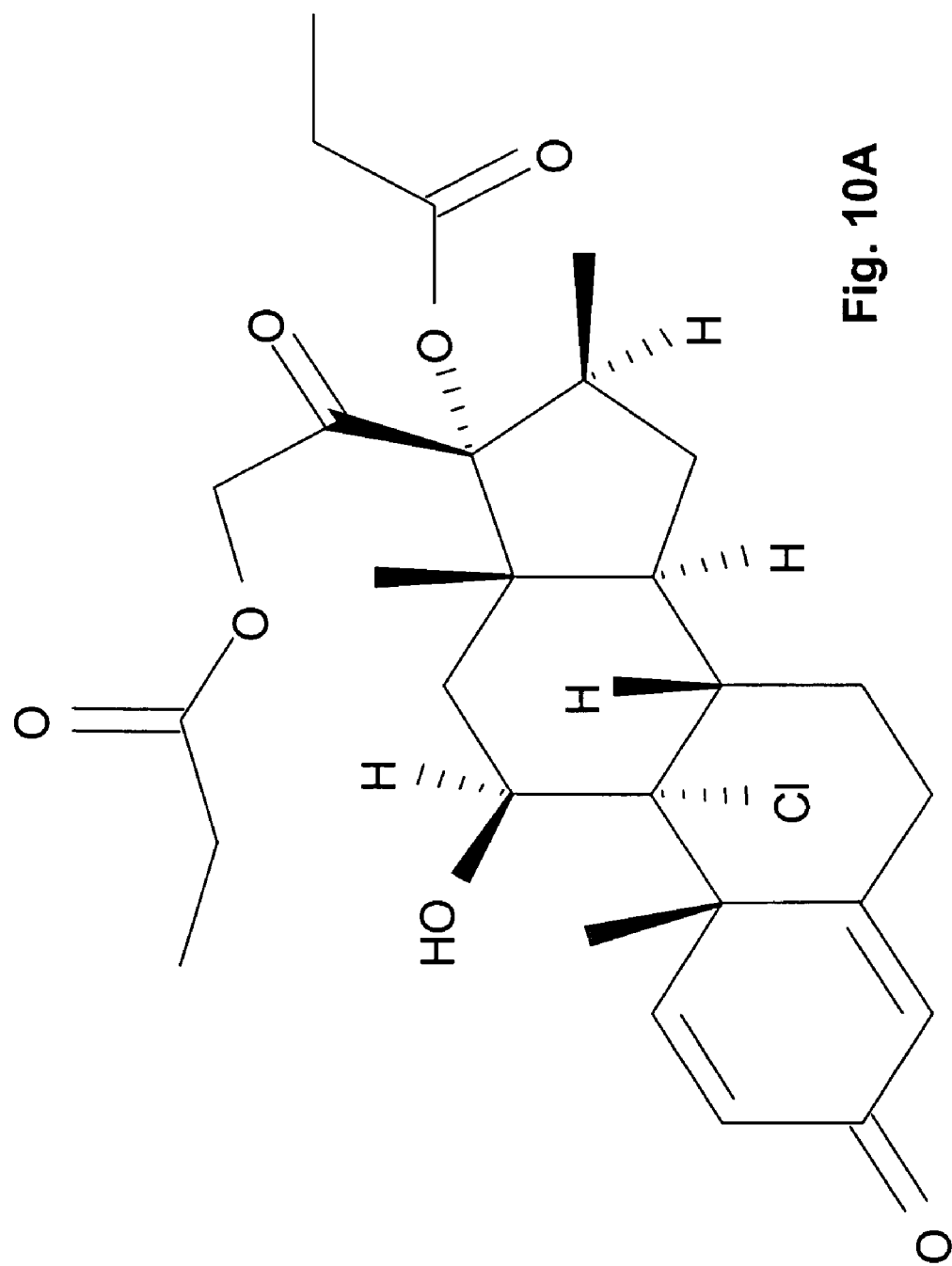
Figure 12B:
Figure 12A:
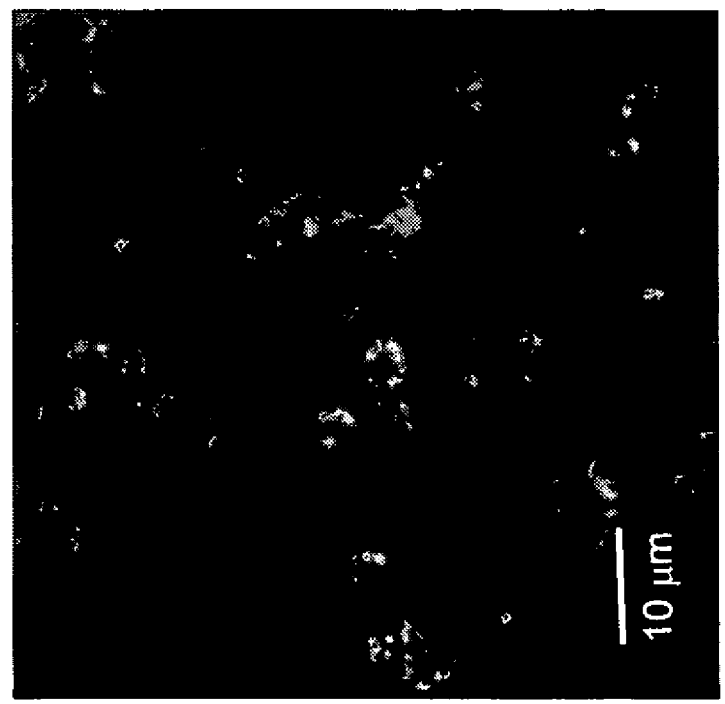
Figure 13B:
Figure 13A:
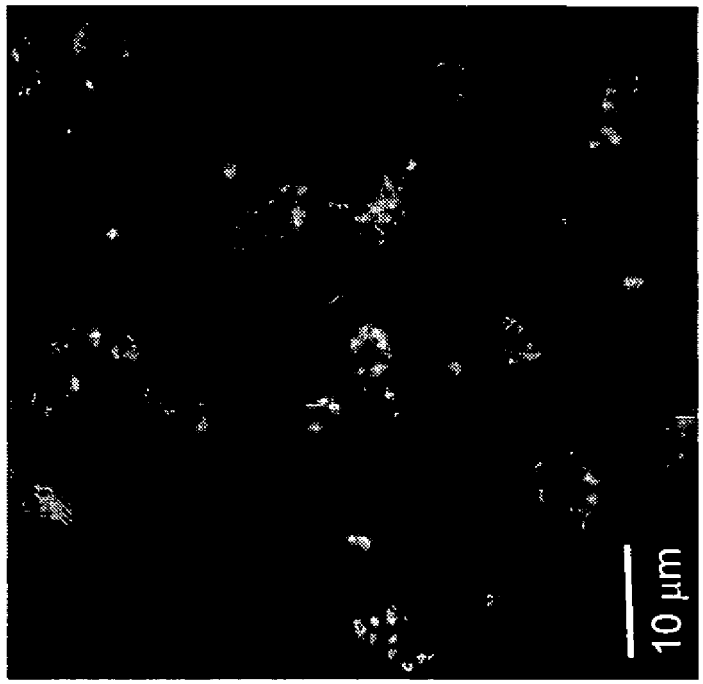
Figure 13C:
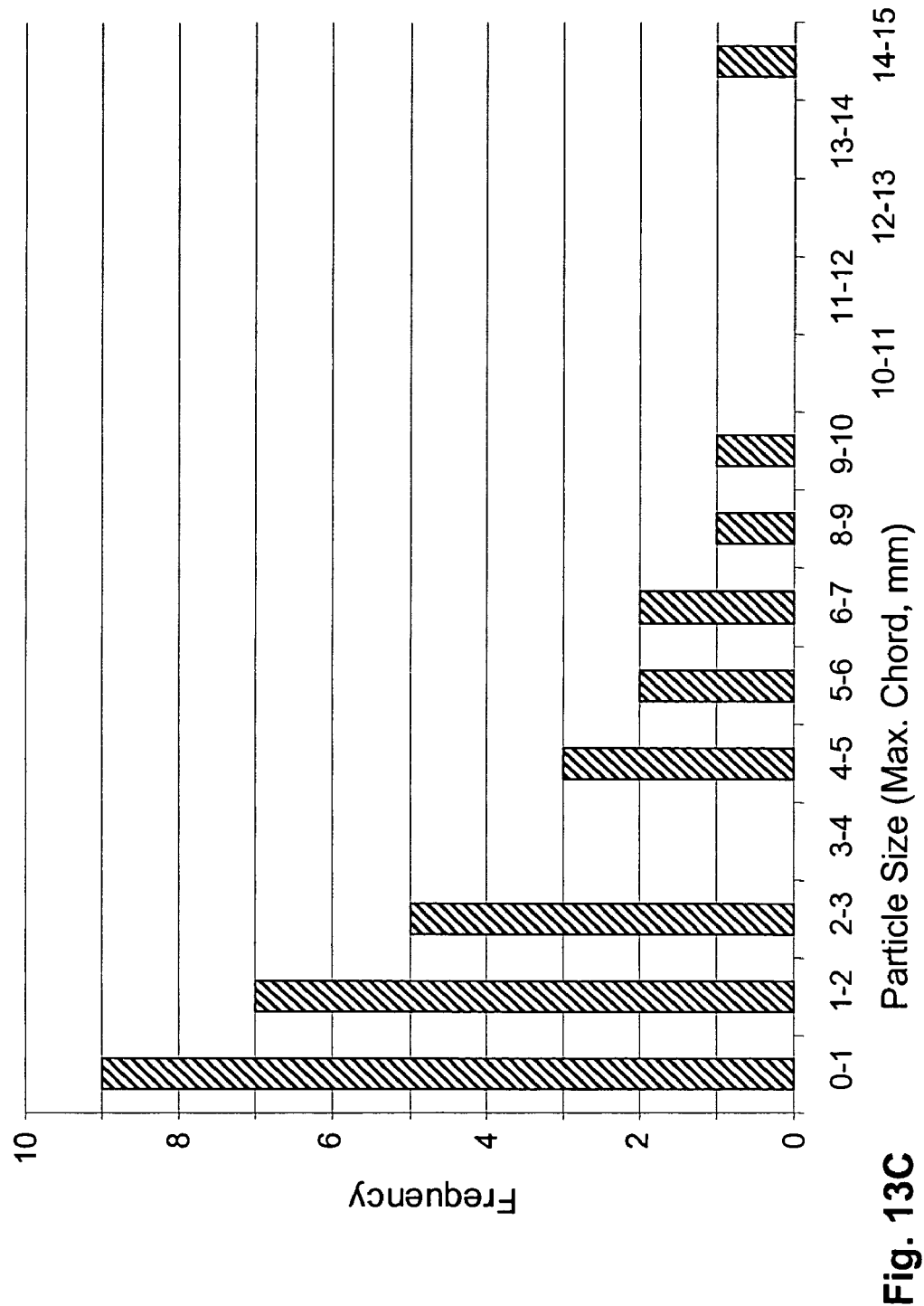
Figure 14B:
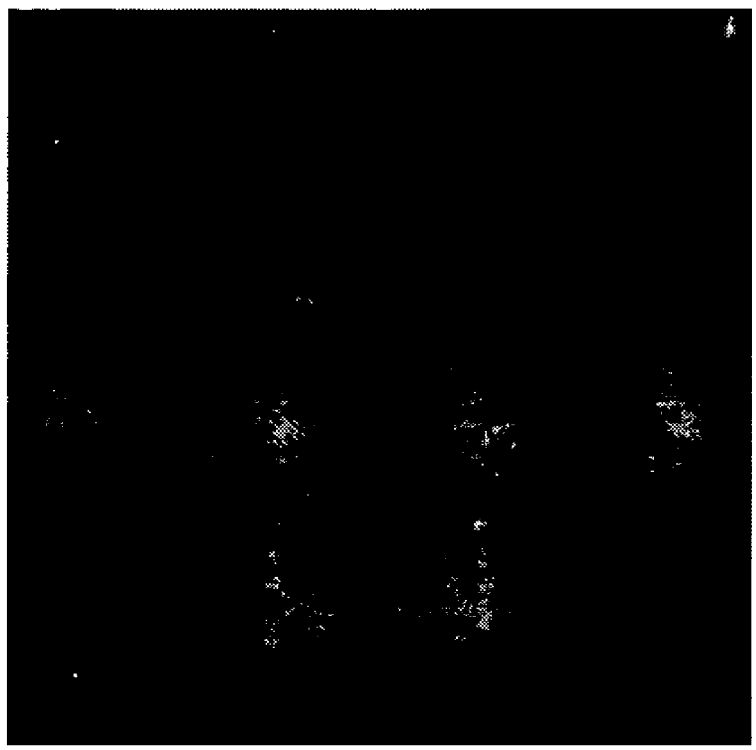
Figure 14A:
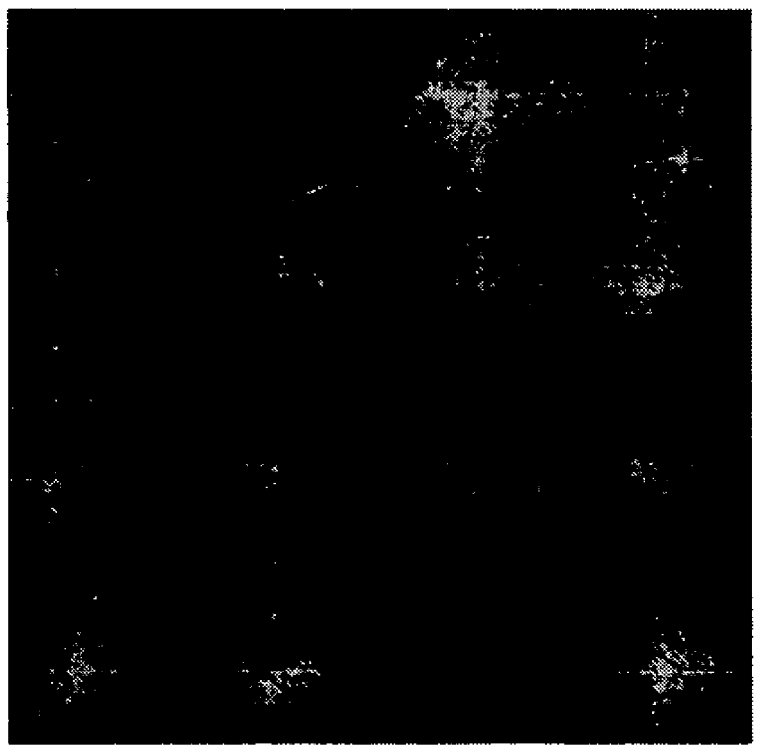
Figure 14C:
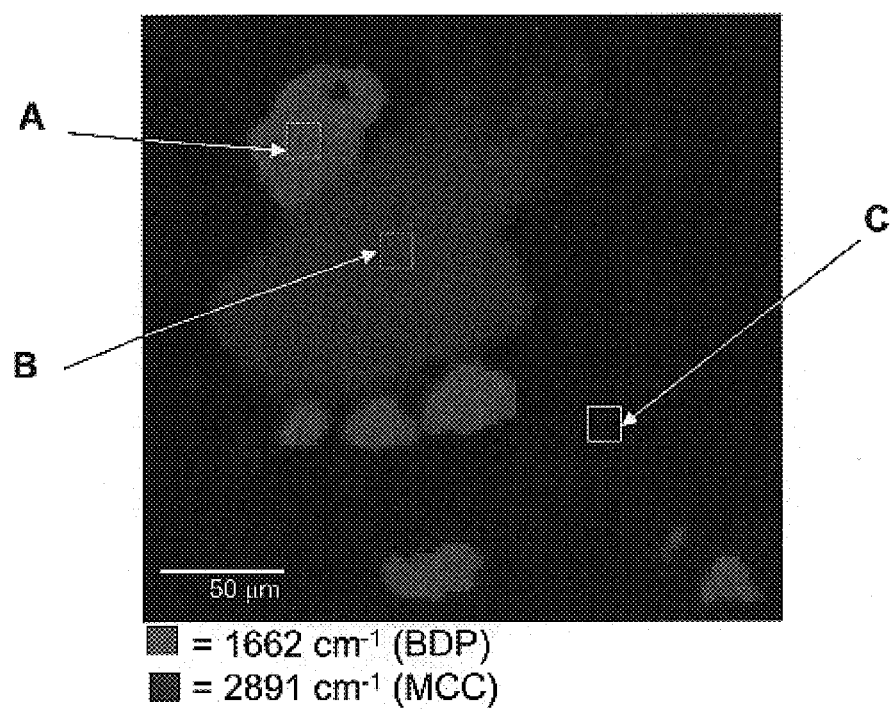
Figure 14D:
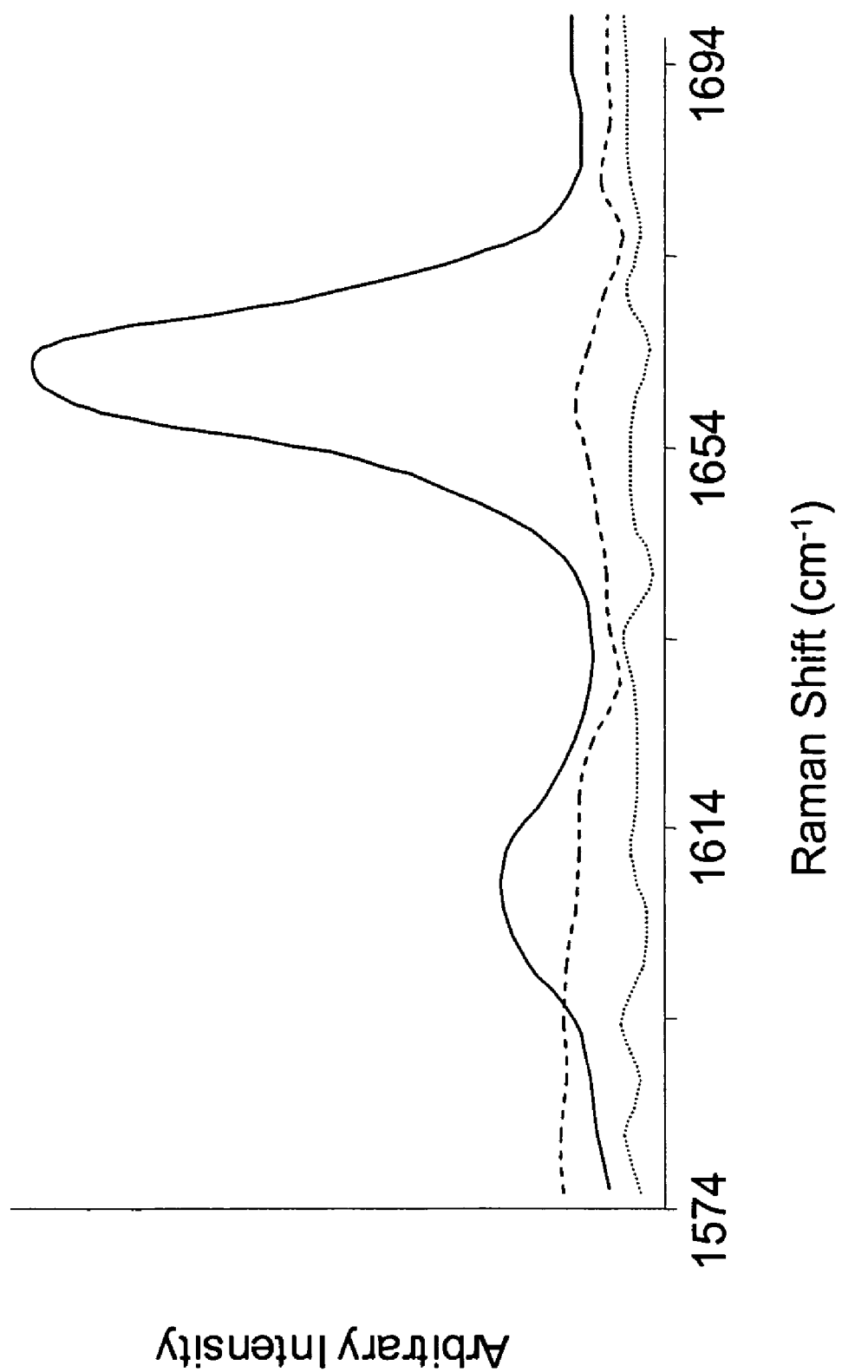

FIGS. 12 and 13 depict a polarized light micrograph and a corresponding binarized image of micronized BDP and geometric properties calculated for 31 particles calculated from the binarized image using a commercial software package. The mean BDP particle size was determined to be 3.02±3.16 micrometers in diameter. The PSD is shown graphically in FIG. 13.

FIGS. 14 through 16 relate to experiments performed with a blend of micronized BDP and MCC in the dry state. The sample was prepared by placing a mixture of BDP and MCC (approximately 20:80 BDP:MCC by volume) on a glass microscope slide. It is expected that the crude nature of the sample preparation resulted in formation of relatively large aggregates of BDP and MCC.

FIG. 14 depicts brightfield reflectance image and polarized light images (FIGS. 14A and 14B, respectively) and a composite Raman chemical image (FIG. 14C) of the BDP/MCC mixture. The polarized light image reveals the birefringent nature of both components in the mixture. The channels of the composite Raman chemical image corresponding to BDP (1 in FIGS. 14C through 14E) and MCC (2 in FIGS. 14C through 14E) are indicated. These results indicate that BDP and MCC domains and background areas (3 in FIGS. 14C through 14E) exhibit characteristic Raman spectral signatures.

Figure 15B:
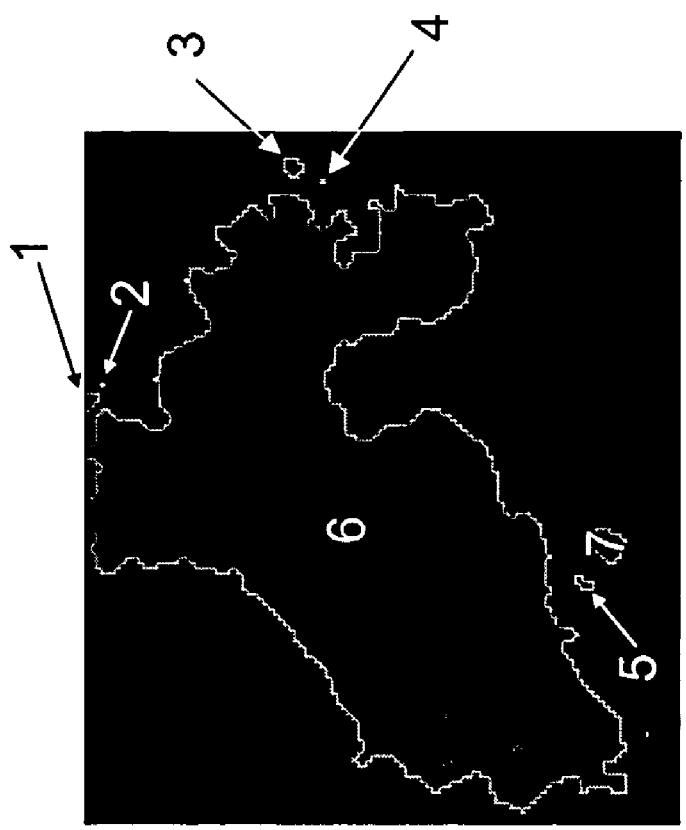
Figure 15A:
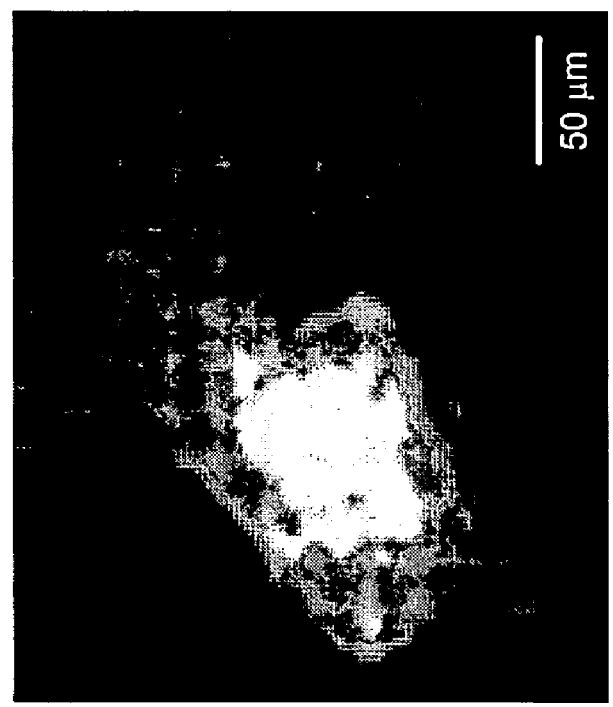

FIG. 15 shows a grayscale Raman image (FIG. 15A), a binary image (FIG. 15B) and PSD table associated with the MCC aggregates in the field of view. Due to the large aggregate in the field of view surrounded by several, much smaller aggregates, the average MCC "particle" (more likely an agglomerate) size was 33.91±71.45 micrometers.

Figure 16B:
Figure 16A:
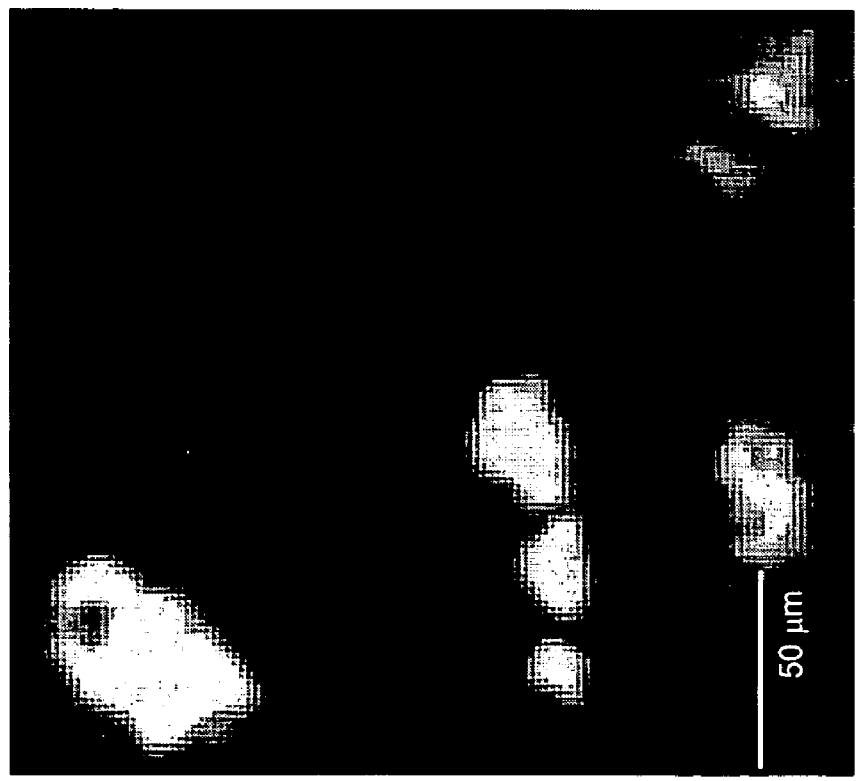
Figure 17B:
Figure 17A:
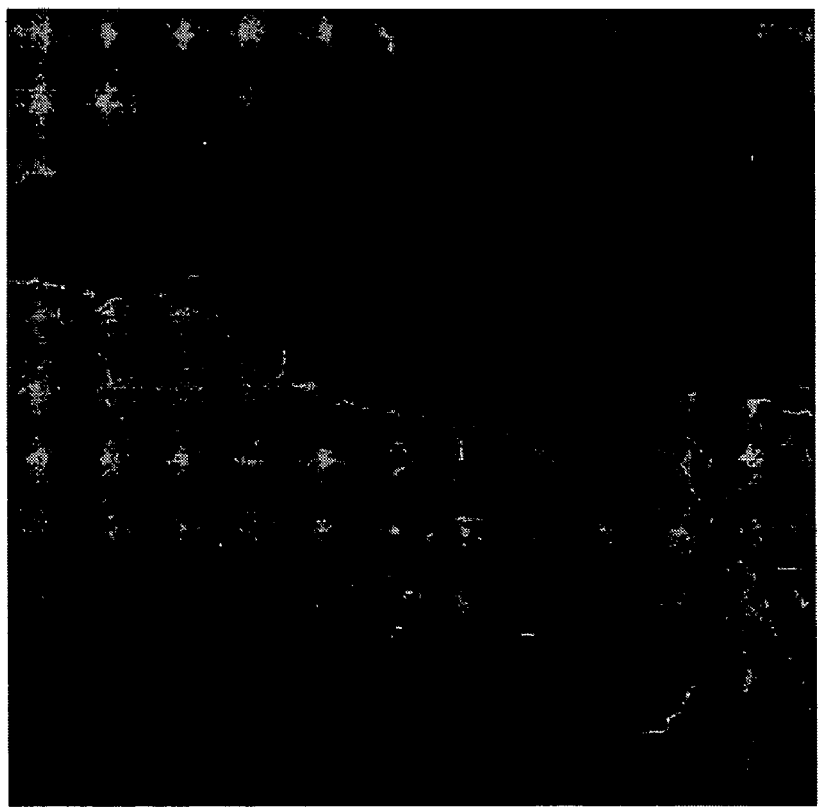
Figure 17C:
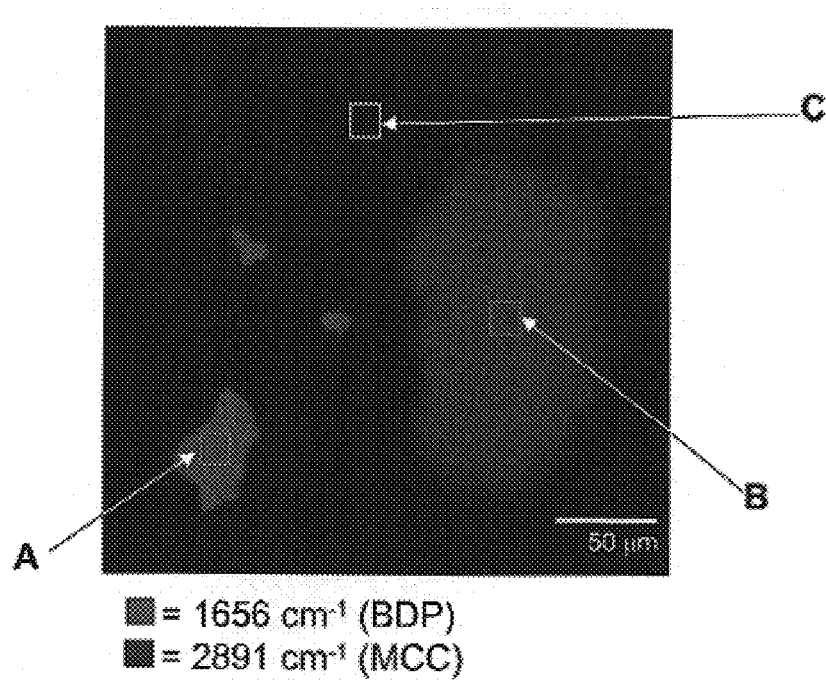
Figure 17D:
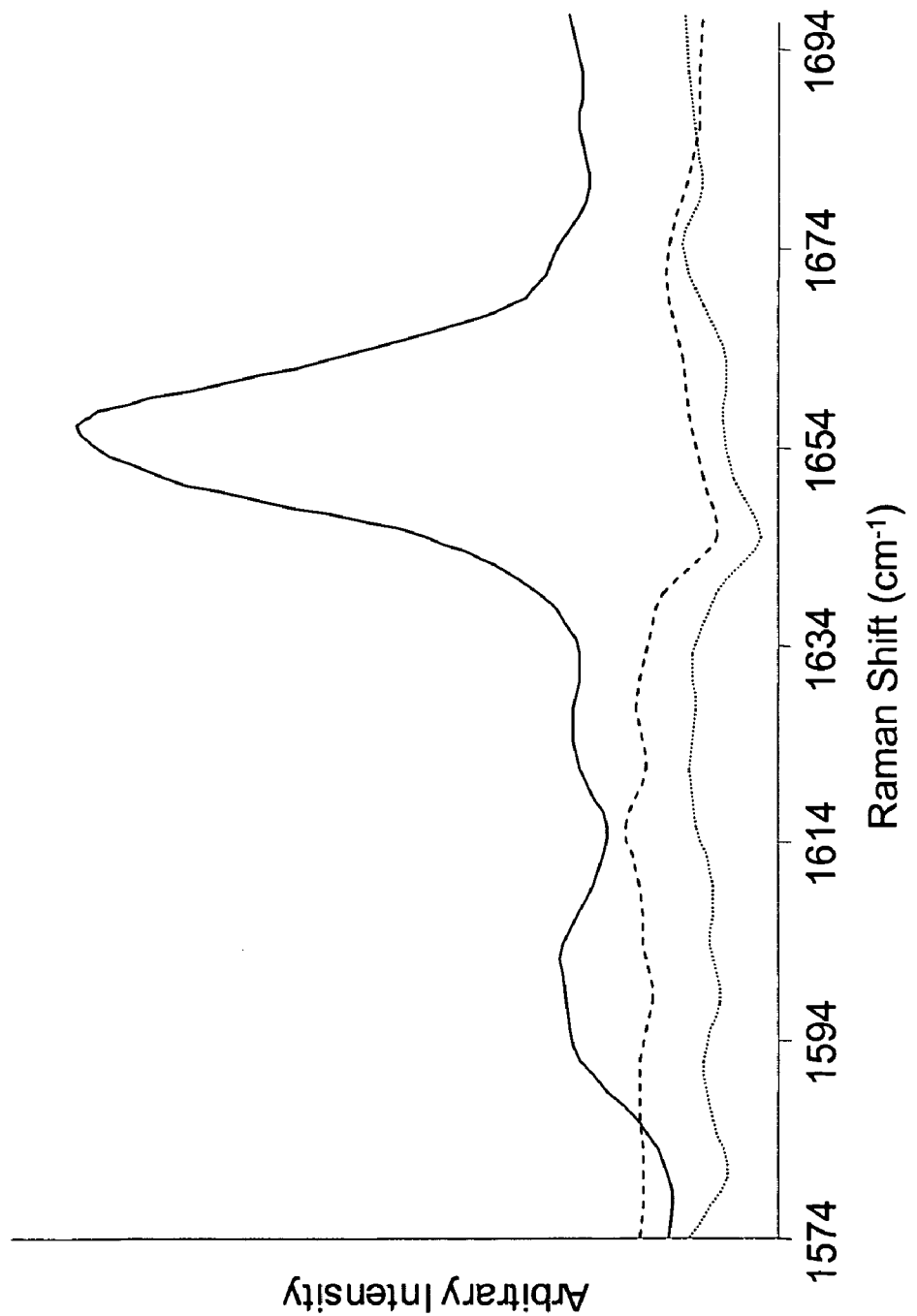
Figure 17E:
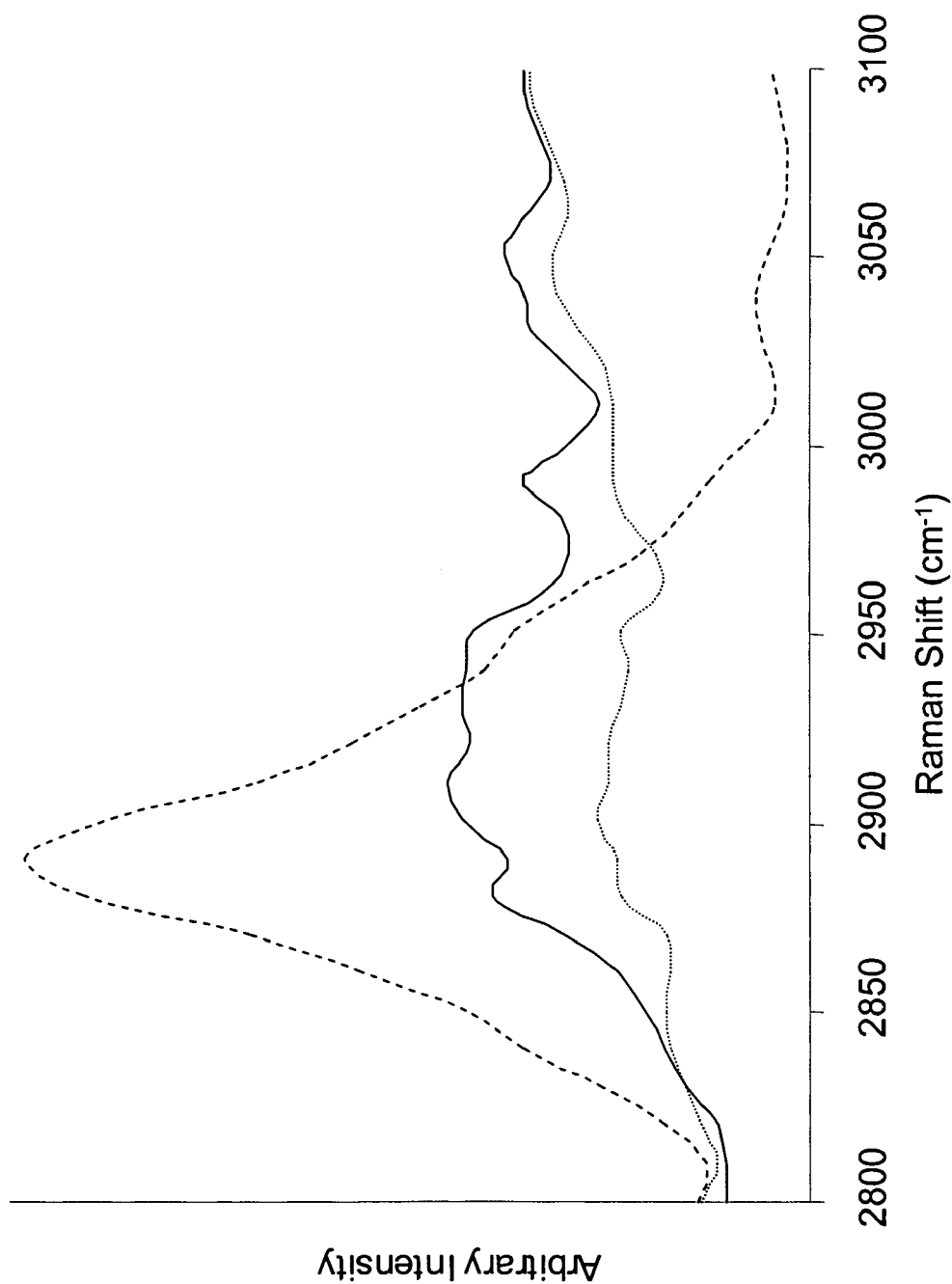

FIG. 16 shows a grayscale Raman image (FIG. 16A), a binary image (FIG. 16B) and a PSD table associated with the BDP aggregates in the field of view. The average BDP "particle" (more likely an agglomerate) size was determined to be 36.99±19.27 micrometers. These results illustrate the ability of the technology to differentiate and identify a drug substance from excipients and the utility of the software to assess particle size of individual domains that exist in the field of view.

FIGS. 17 through 19 demonstrate the ability of these methods to identify drug substance and determine particle size and PSD of drug substance in a blend of micronized BDP and MCC following the addition of water. A small aliquot (approximately 10 microliters) of distilled water was introduced into the dry BDP/MCC mixture used in the experiments corresponding to FIGS. 14 through 16 using a microsyringe manually guided while viewing through the FALCON Microscope with the CCD video camera. Manually controlling delivery of the water to the sample on a microscope scale was challenging. The addition of water caused particles to move out of the field of view while new ones moved into the field of view, which made it difficult to make an accurate comparison of particle statistics before and after the addition of water.

FIG. 17 shows a brightfield reflectance image (FIG. 17A), a polarized light image (FIG. 17B), and a composite Raman chemical image (FIG. 17C) of the BDP/MCC mixture following addition of water. The green and blue color channels of the composite Raman chemical image have been color-coded for BDP and MCC, respectively. The channels of the composite Raman chemical image corresponding to BDP (1 in FIGS. 17C through 17E) and MCC (2 in FIGS. 17C through 17E) are indicated. These results indicate that BDP and MCC domains and background areas (3 in FIGS. 17C through 17E) exhibit characteristic Raman spectral signatures.

Figure 18B:
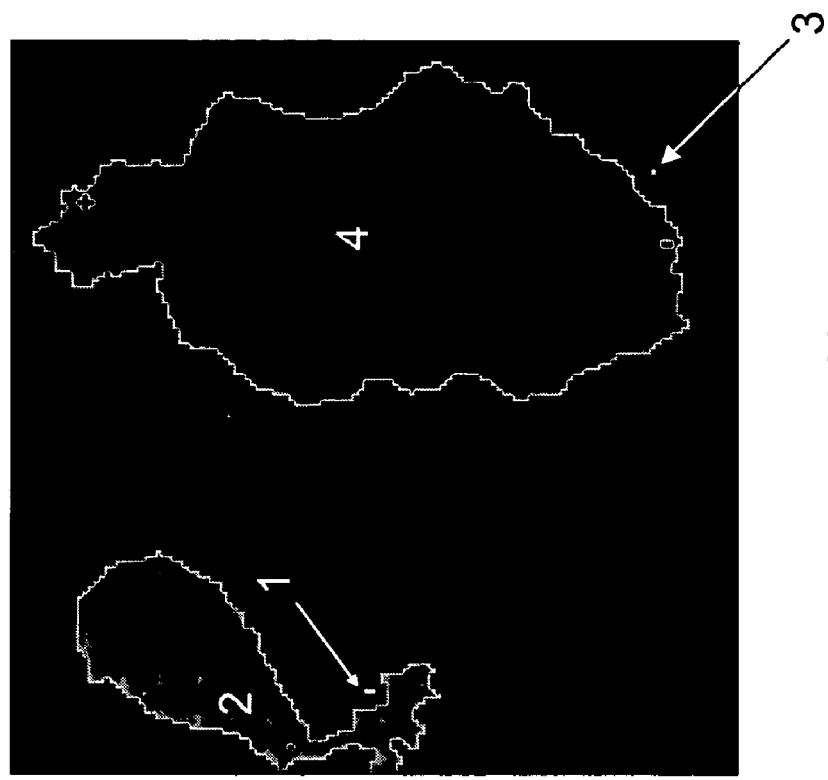
Figure 18A:
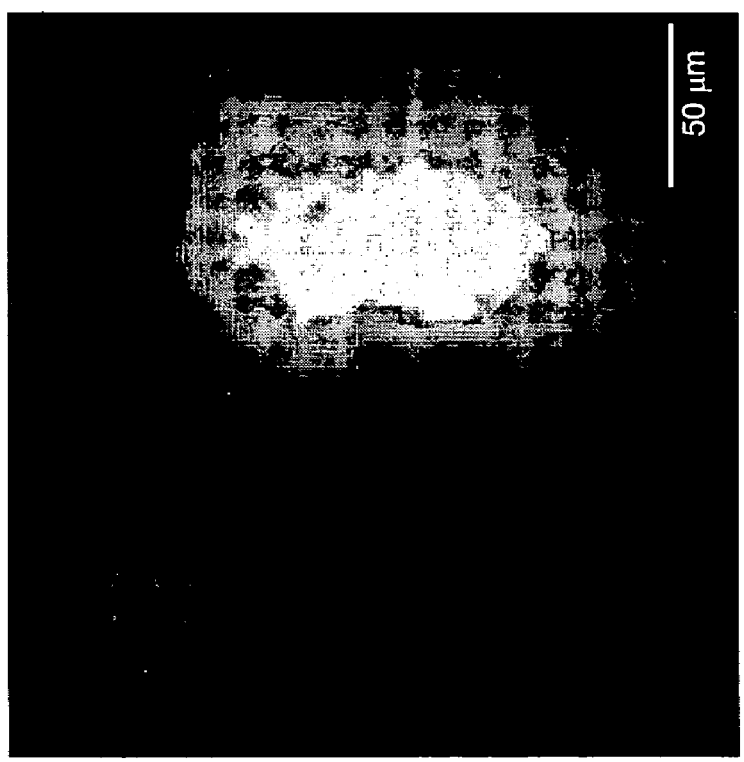

FIG. 18 shows a grayscale Raman image (FIG. 18A), a binary image (FIG. 18B) and PSD table associated with the MCC aggregates in the field of view following addition of water. Due to the large aggregate in the field of view surrounded by several, much smaller aggregates, the average MCC "particle" (more likely an agglomerate) size was 48.75±57.57 micrometers in diameter.

Figure 19B:
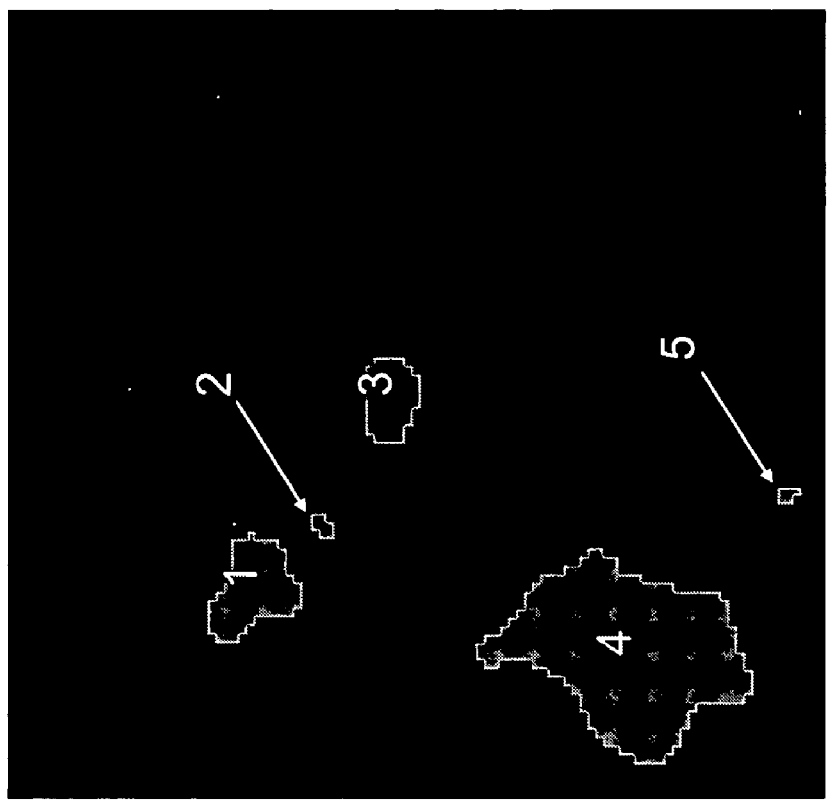
Figure 19A:

FIG. 19 shows a grayscale Raman image (FIG. 19A), a binary image (FIG. 19B) and PSD table associated with the BDP aggregates in the field of view. The average BDP "particle" (more likely an agglomerate) size was determined to be 13.80±14.25 micrometers in diameter.

Figure 20B:
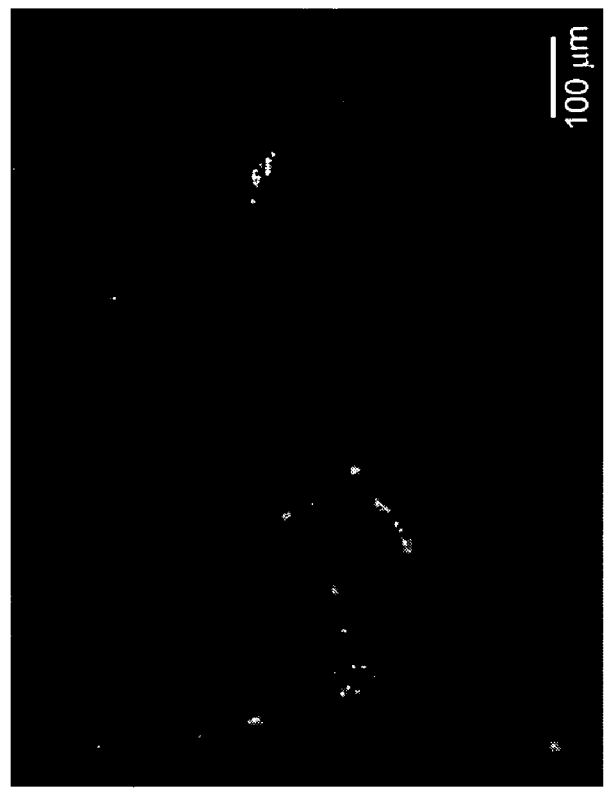
Figure 20A:
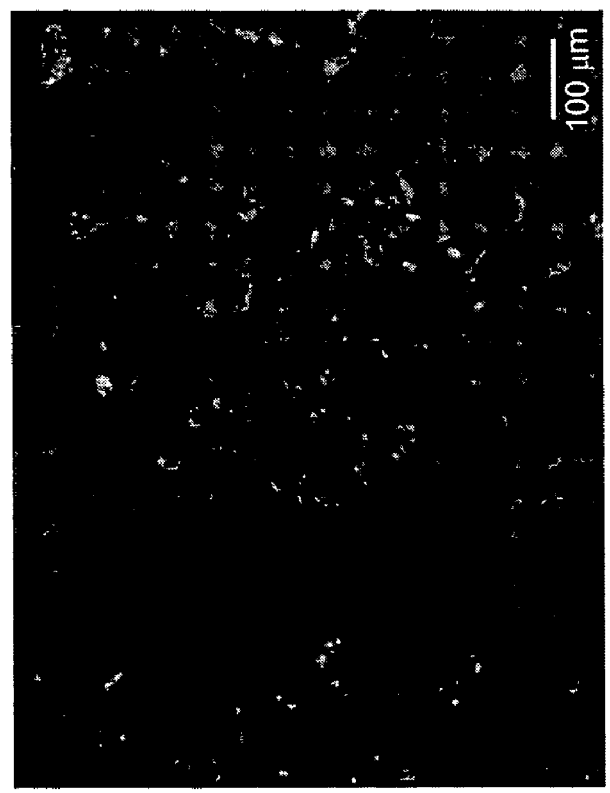
Figure 21B:
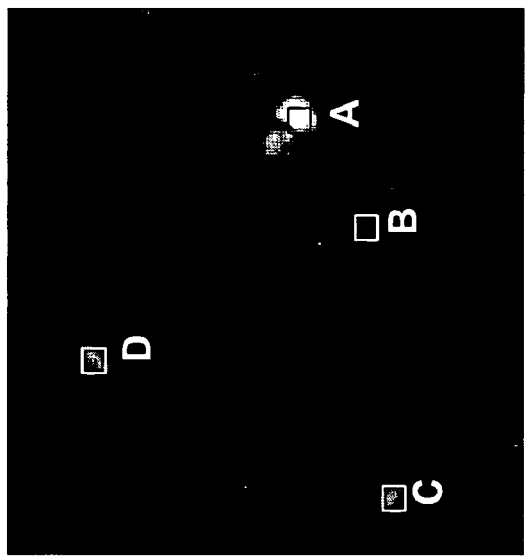
Figure 21C:
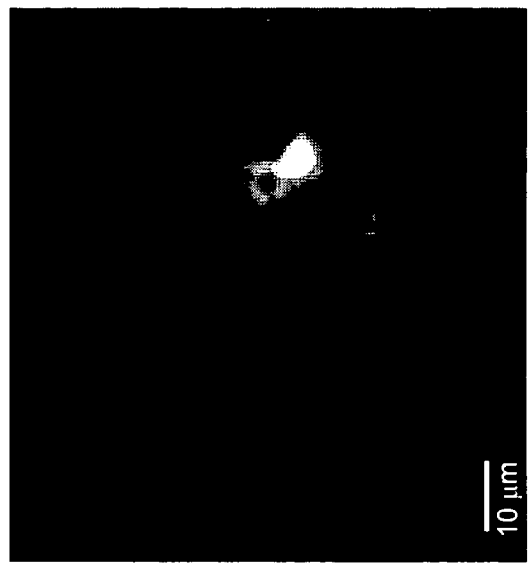
Figure 21A:
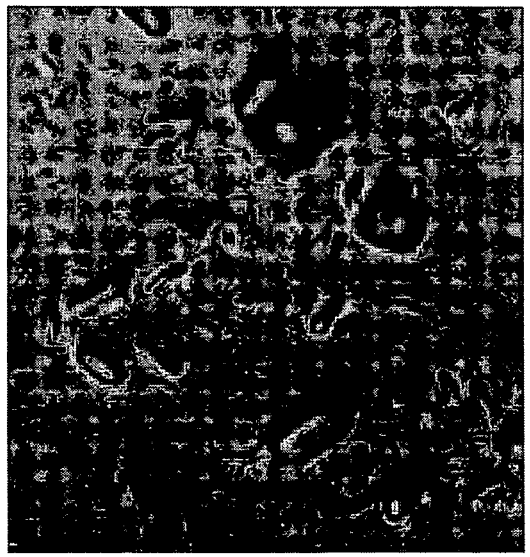
Figure 21D:
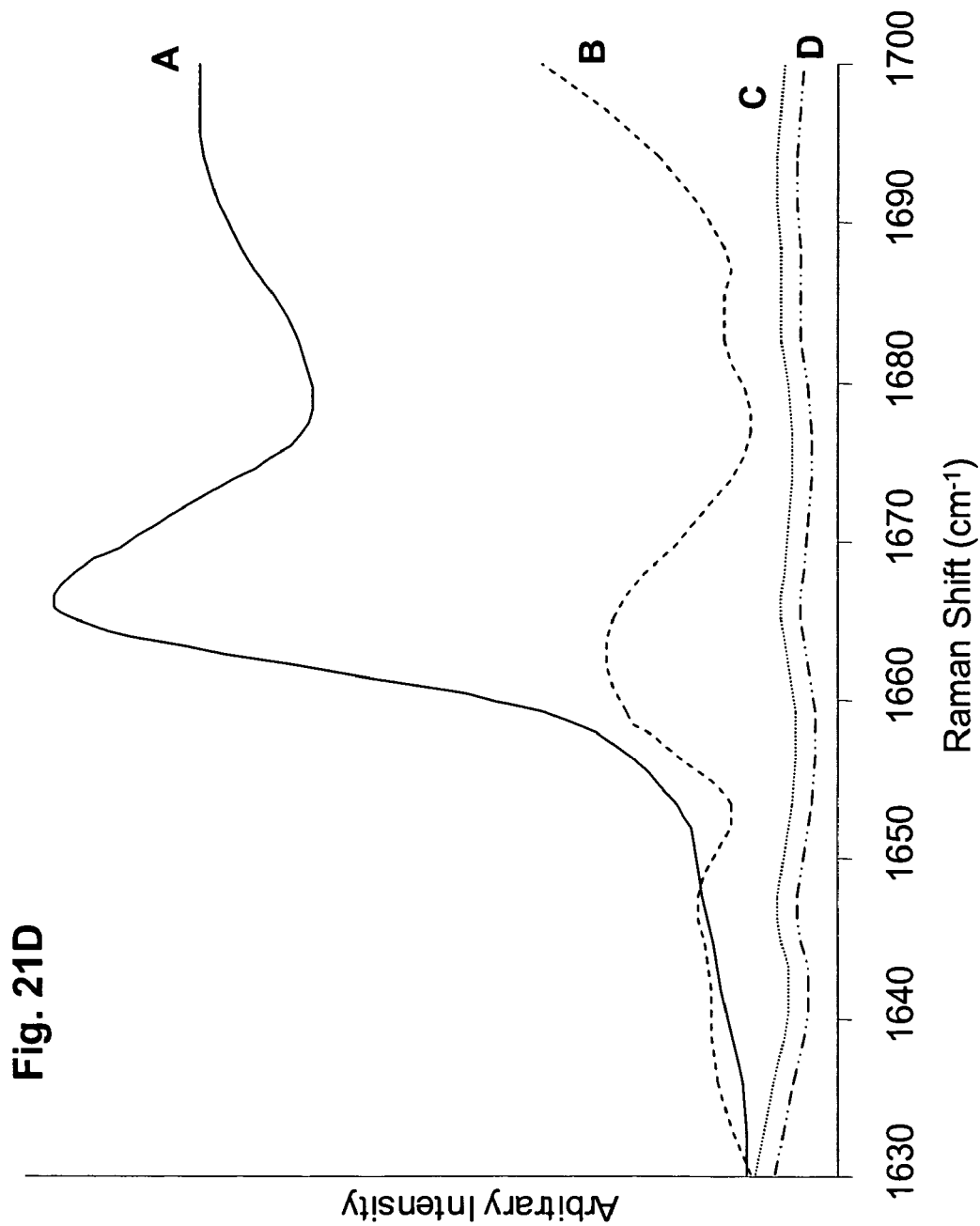
Figure 21E:
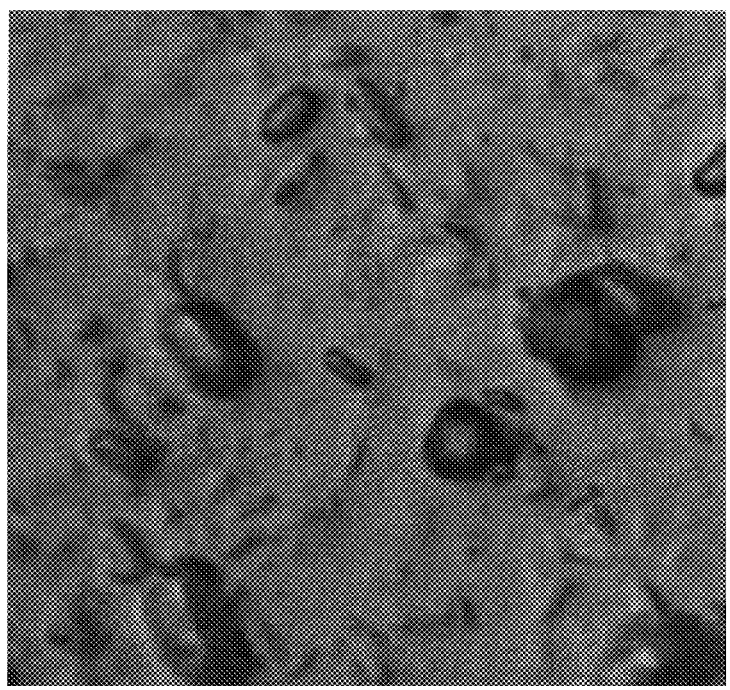
Figure 22B:
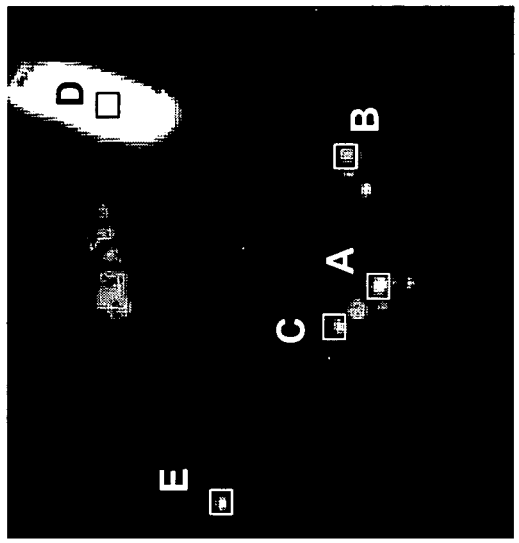
Figure 22C:
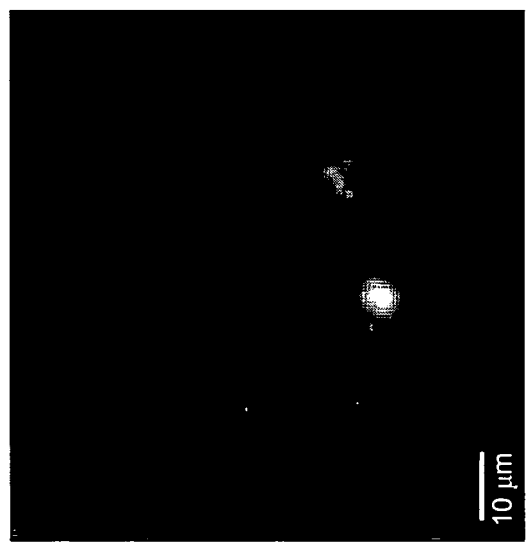
Figure 22A:
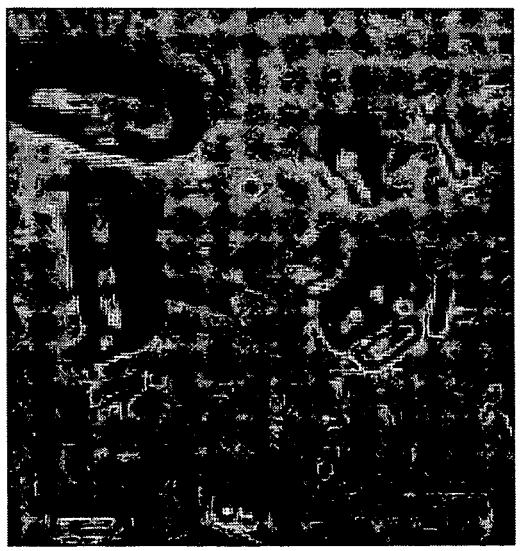
Figure 22E:
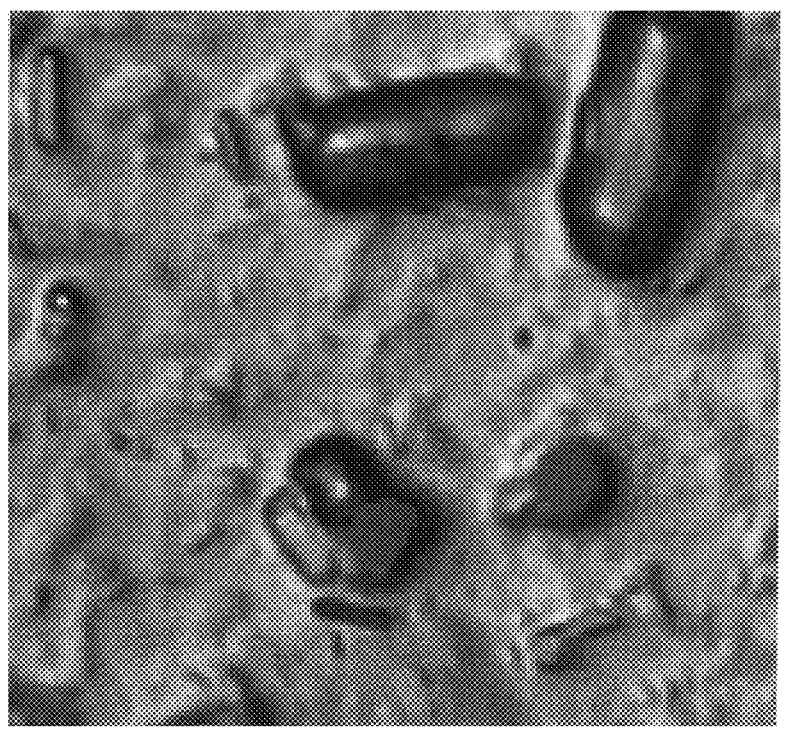
Figure 23A:
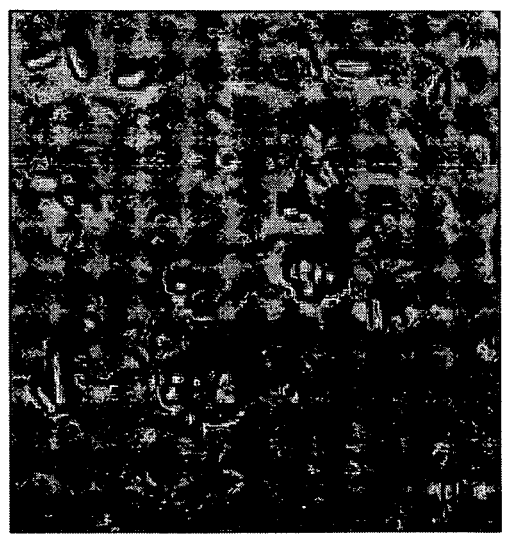
Figure 23B:
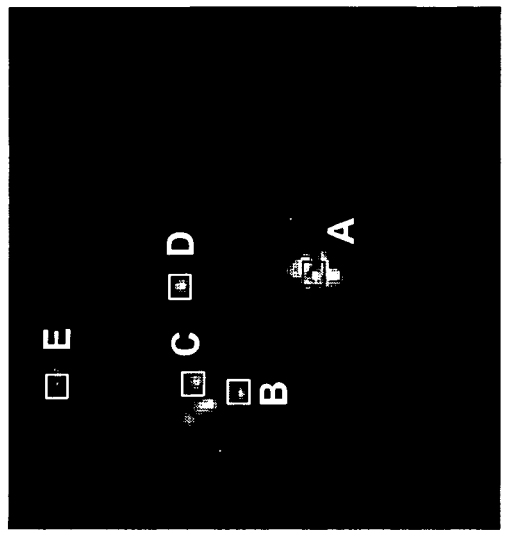
Figure 23C:
Figure 23E:
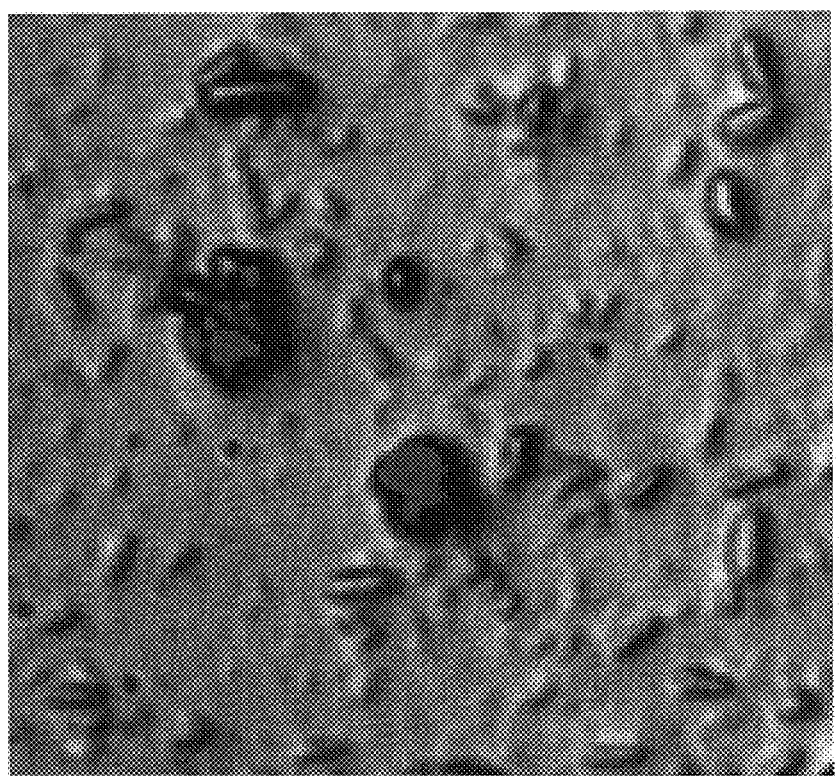
Figure 24B:
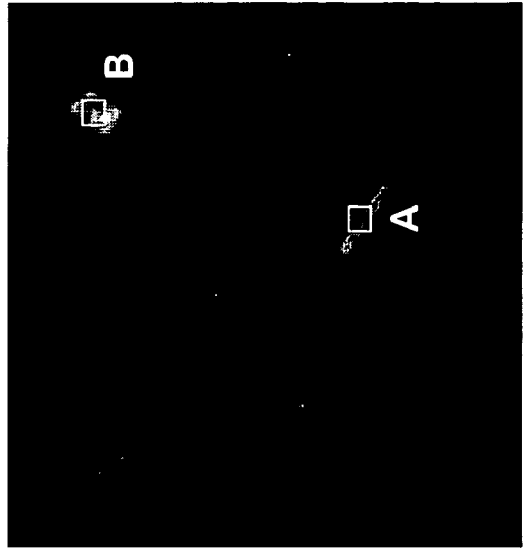
Figure 24C:
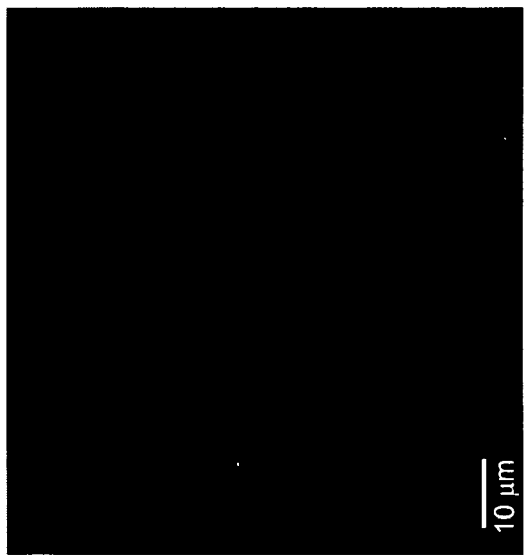
Figure 24A:
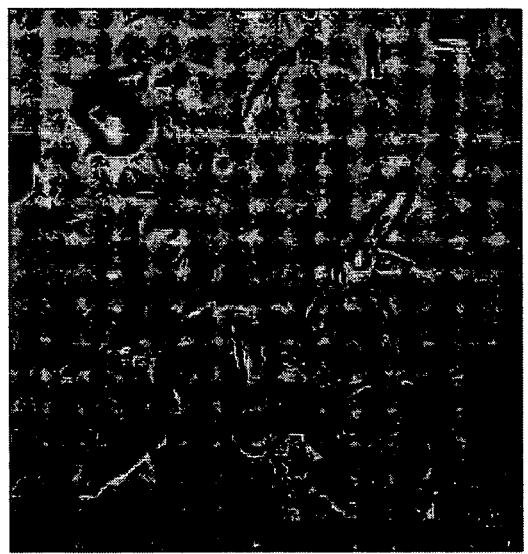
Figure 24D:
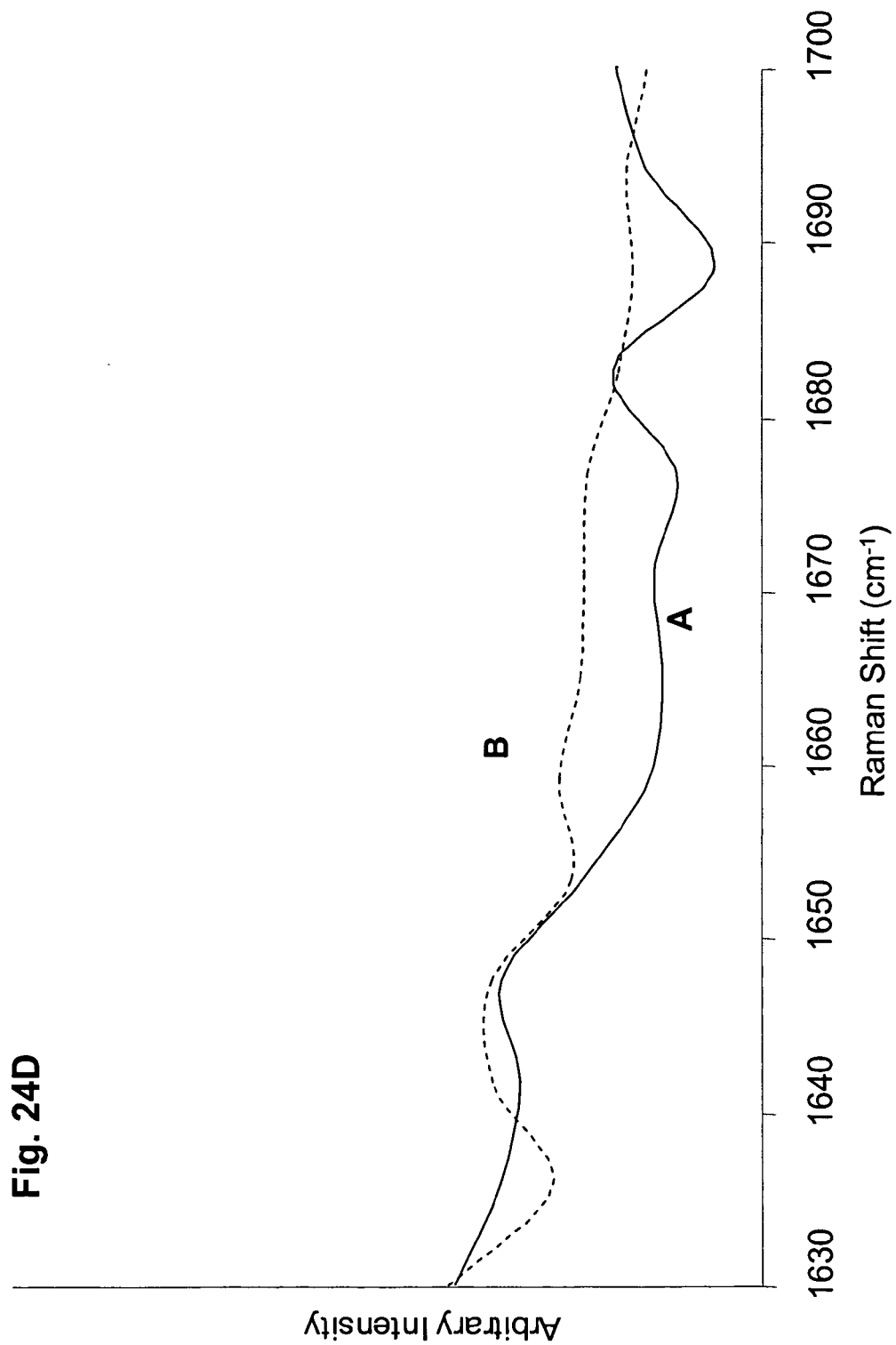

FIG. 20 shows a polarized light image of the MCC/BDP blend prior to the addition of water (FIG. 20A) and a polarized light image of the MCC/BDP blend following addition of water (FIG. 20B).

To address issues associated with sample preparation (i.e., aggregate formation in the BDP/MCC blends) and the dynamic nature of an aqueous blend, RCI was performed on two nasal spray samples—one of which (BECONASE AQ (™)) contained the active pharmaceutical ingredient (BDP) and the other of which was a placebo sample. Samples were prepared by shaking, priming, and spraying each nasal spray sample onto respective aluminum-coated glass microscope slide positioned in an upright position approximately 6 inches away. The samples were then immediately turned right-side-up and allowed to dry. Aluminum-coated glass microscope slides were used to minimize background fluorescence arising from any rare-earth elements present in the glass substrates.

Figure 25A:
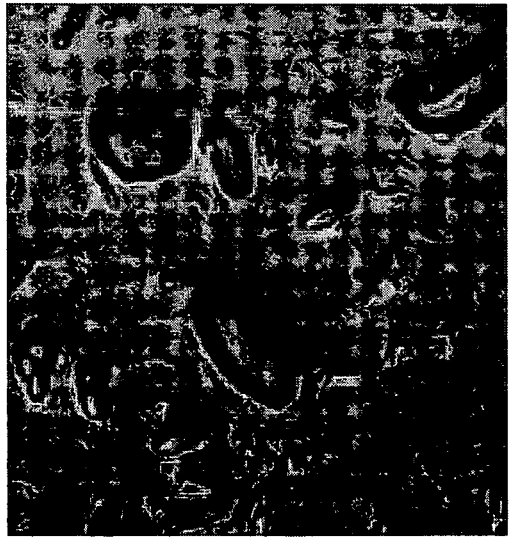
Figure 25B:
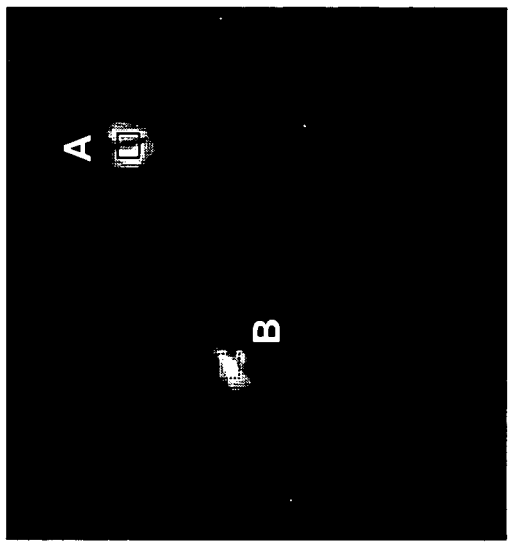
Figure 25C:
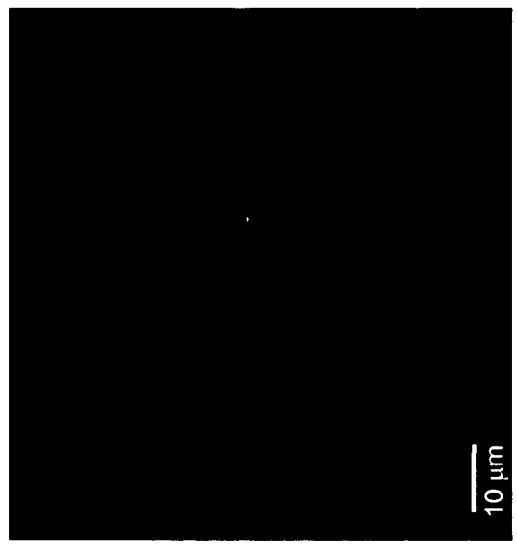

FIGS. 21 through 23 are RCI results from 3 regions of interest (ROIs) from the BECONASE AQ (™) nasal spray sample containing BDP. FIGS. 24-26 are RCI results from 3 ROIs from the placebo nasal spray sample. Each of FIGS. 21A, 22A, 23A, 24A, 25A, and 26A depicts a brightfield reflectance image of the respective sample. Each of FIGS. 21B, 22B, 23B, 24B, 25B, and 26B depicts a polarized light image of the respective sample. Each of FIGS. 21C, 22C, 23C, 24C, 25C, and 26C depicts a Raman chemical image of the respective sample. Each of FIGS. 21D, 22D, 23D, 24D, 25D, and 26D depicts Raman spectra of the regions indicated in the corresponding FIGS. 21C, 22C, 23C, 24C, 25C, and 26C. Each of FIGS. 21E, 22E, and 23E depicts an overlay of the brightfield and RCI images of corresponding FIGS. 21A/21C, 22A/22C, and 23A/23C.

The characteristic Raman properties of BDP could be detected in each of the BECONASE AQ-containing samples and that those BDP-specific Raman properties were not observed for other components in the sample. Brightfield/Raman overlay images indicated what appears to be adsorption of BDP to one or more excipients in the nasal spray sample. These results indicate that the methods described herein can be used to characterize properties of drug compositions beyond geometric properties and including such factors as particle agglomeration. Such agglomeration is important, because the association of an active ingredient with a second compound can reduce the ability of the active ingredient to dissolve, the effectiveness of the active ingredient, the ability of a particle including the active ingredient to travel to a body location, or another relevant pharmacological property of the active ingredient.

Figure 27C:
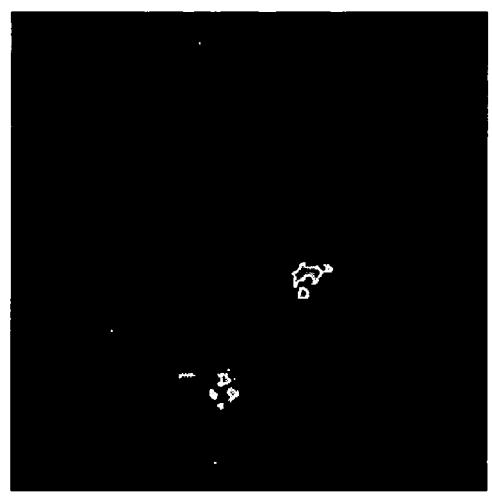
Figure 27B:
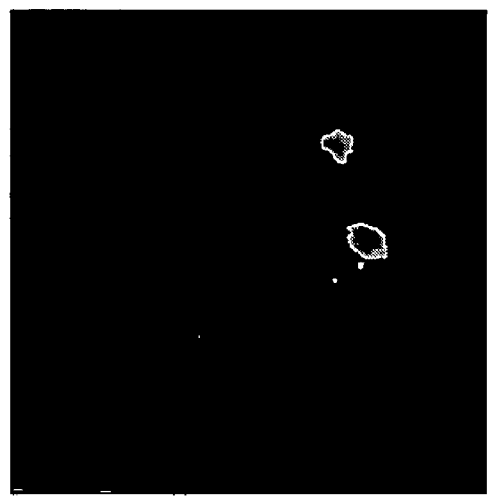
Figure 27A:
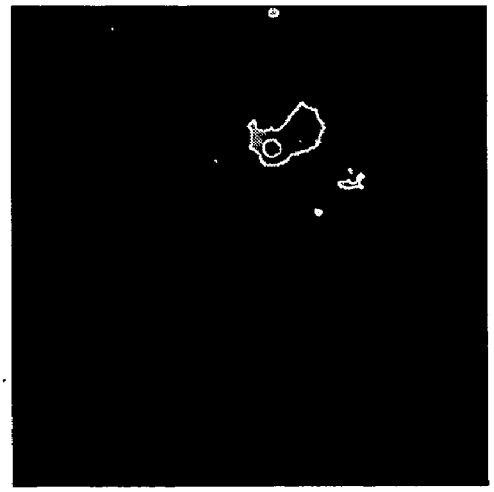
Figure 28:
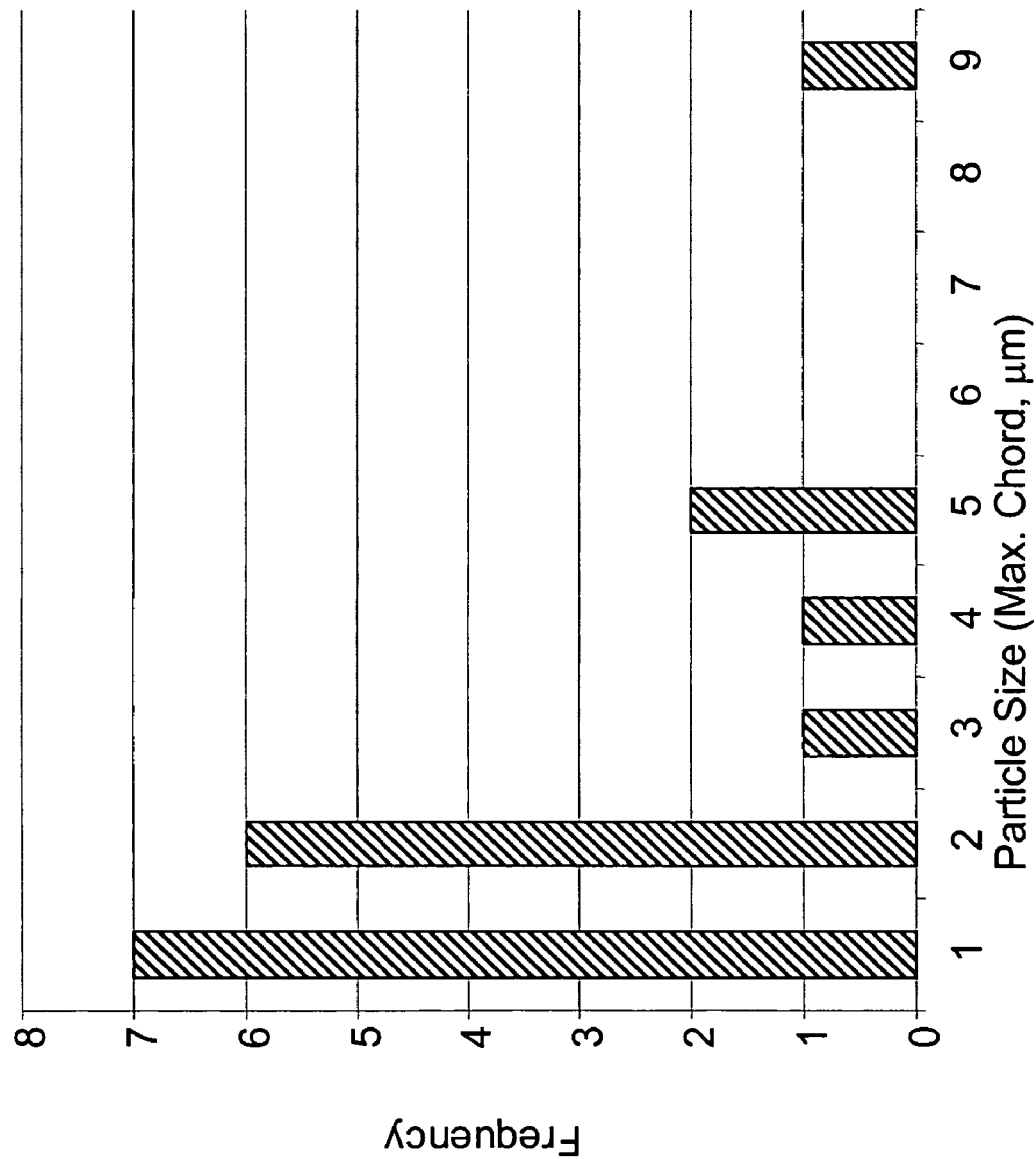

FIGS. 27 and 28 relate to experiments in which particle size and PSD of BDP were assessed for the BECONASE AQ (™) drug product. FIGS. 27A-27C and 28A-28C depict binary images and associated particle statistics for BDP particles detected by RCI in three ROIs of the dried BECONASE AQ (™) sample. A PSD table is shown in FIG. 27 and a graphical representation of PSD is shown in FIG. 28.

The result of the experiments described in this example indicate that particle size, chemical identity, and PSD characteristics of corticosteroids in aqueous suspension of nasal sprays using RCI can be measured using the methods described herein. Raman dispersive spectral library results demonstrate the amenability of Raman spectroscopy and RCI to be used as characterization tools for aqueous suspensions of nasal sprays. RCI results demonstrated the ability to differentiate and identify the chemical make-up of multiple components in complex BDP sample and placebo mixtures. PSD measurements made on binary polarized light microscope images of the neat drug dispersed on a glass microscope slide revealed a mean particle size of 3.02±3.16 micrometers. PSD measurements performed on binary Raman images of BDP/MCC mixtures revealed mean particles sizes of 33.91±71.45 micrometers and 36.99±19.27 micrometers for MCC and BDP, respectively, before the addition of water and 48.75±57.57 micrometers and 13.80±14.25 micrometers for MCC and BDP, respectively, following the addition of water. The large mean PSDs relative to the pure, neat drug are a result of particulate conglomerations. The difference in the mean particle sizes before and after the addition are likely due to the movement of particles into and out of the field of view rather than changes to particle size resulting from the addition of water. PSD measurements performed on binary Raman images of the BDP distribution in BECONASE AQ (™) nasal spray samples revealed a mean particle size of 1.79±1.33 micrometers. As expected, there were no BDP particles detected in the placebo. Brightfield/Raman overlay images revealed what appears to be the adsorption of BDP to one or more excipients in the nasal spray sample.

Example 2

Particle Size Standard Testing Blind Study

The experiments in this example were performed to demonstrate the validity of RCI for small particle sizing in a blinded study.

Six different polystyrene microsphere particle size standards were combined in a sample. Using optical microscopy and RCI, the mean particle size and associated standard deviations were determined for each size standard following a method consistent with the Duke Scientific (DS) method for size determination.

The DS method was performed as follows. Highly uniform microspheres, when placed on a flat surface such as a glass microscope slide, tended to form systematic hexagonal arrays. Using optical microscopy, the sizes were determined by measuring many polystyrene microspheres in a row and dividing by the number of spheres. The results were then verified by NIST. This method was developed due to the difficulty in determining the edge of the spherical particle especially when approaching the diffraction limit of light. In addition, this method is less susceptible to distorted measurements attributable to misshaped and undersized/oversized microspheres since these outliers tend to disrupt an ordered array which can be microscopically observed and avoided.

Standards were prepared by placing small drops of each of the size standard solutions on standard glass microscope slides, dispersing the solution evenly by sliding across it with another microscope slide and allowing the solution to dry. Optical microscopy and RCI data was collected for regions of interest for each size standard.

Figure 29B:
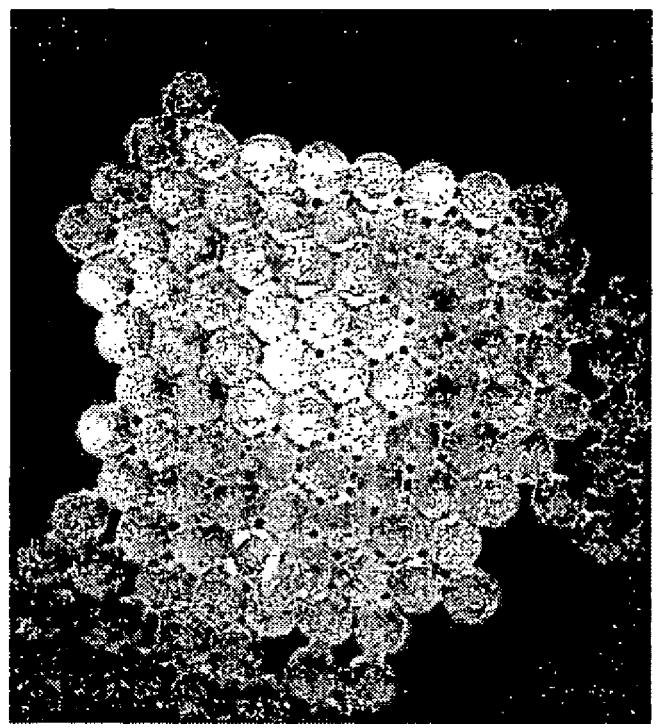
Figure 29A:
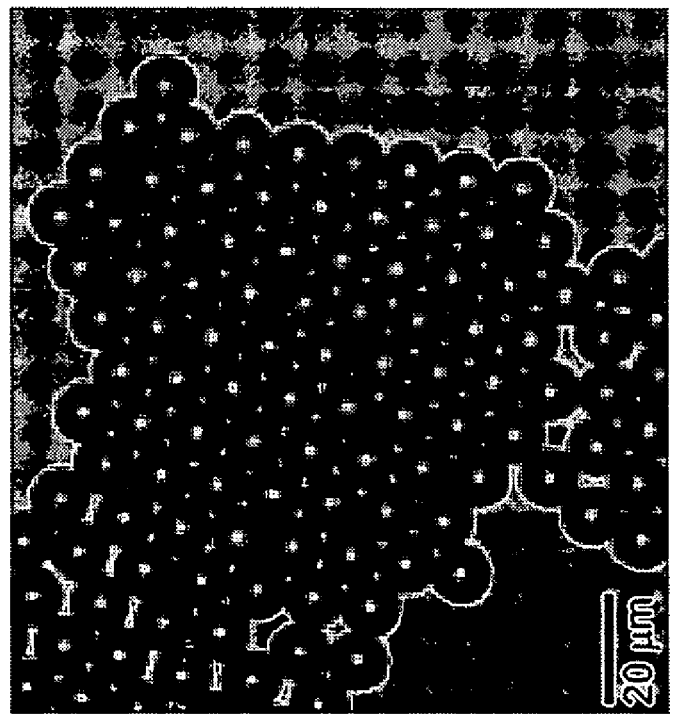
Figure 29C:
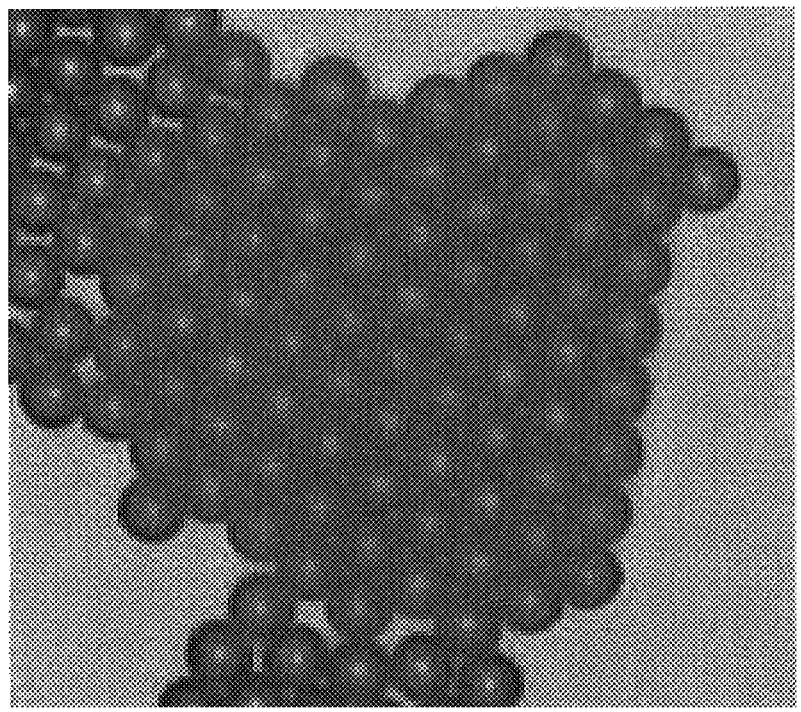

FIG. 29 shows a brightfield reflectance image (FIG. 29A), a Raman chemical image (FIG. 29B) and a brightfield/Raman overlay image (FIG. 29C) of the 10 micron NIST-traceable polystyrene microsphere particle size standards arranged in a hexagonally close-packed arrangement. Similar data was acquired for the remaining five size standards.

The table provided in Figure compares the results using the DS method to the NIST traceable values. The array method results on the RCI data are within statistical agreement to the accepted values for the NIST-traceable standards for those size standards in which a hexagonally close-packed arrangement was obtainable.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of assessing a geometric property of a particle of a substance in a sample, the method comprising irradiating the sample, generating a first image of Raman-shifted radiation scattered from the sample at a Raman shift value characteristic of the substance, and determining the geometric property from the image.

2. The method of claim 1, wherein the image is an image of a microscopic field.

3. The method of claim 1, comprising simultaneously determining the geometric property of multiple particles of the substance in the sample.

4. The method of claim 1, wherein the geometric property is characteristic of the size of the particle.

5. The method of claim 1, comprising generating an image of Raman-shifted radiation scattered from the sample at multiple Raman shift values characteristic of the substance.

6. The method of claim 1, further comprising comparing the first image and a second image of Raman-shifted radiation scattered from the sample at a Raman shift value characteristic of a compound other than the substance.

7. The method of claim 6, wherein the first and second images are combined in an aligned manner.

8. The method of claim 6, comprising determining the geometric properties of the particle of the substance and of a particle of the compound in the sample.

9. The method of claim 1, further comprising comparing the first image and a second image of the sample generated by a spectroscopic method other than Raman spectroscopy.

10. The method of claim 9, wherein the first and second images are combined in an aligned manner.

11. The method of claim 1, wherein the image is a two-dimensional image.

12. The method of claim 11, wherein the geometric property is selected from the group consisting of the area, the perimeter, a Feret diameter, the maximum chord length, a shape factor, and an aspect ratio of the particle.

13. The method of claim 1, wherein the image is a three-dimensional image.

14. The method of claim 13, wherein the geometric property is selected from the group consisting of the volume, the surface area, a Feret diameter, the maximum chord length, a shape factor, and an aspect ratio of the particle.

15. The method of claim 1, wherein the particle is irradiated with substantially monochromatic light.

16. The method of claim 15, wherein the light has a wavelength in the range from 220 to 1100 nanometers.

17. The method of claim 15, wherein the light has a wavelength in the range from 280 to 695 nanometers.

18. The method of claim 15, wherein the light has a wavelength of about 532 nanometers.

19. The method of claim 1, wherein the particle is irradiated with laser light.

20. The method of claim 1, wherein the particle is immobilized prior to generating the image.

21. The method of claim 20, wherein the particle is immobilized by depositing the particle on a surface.

22. The method of claim 20, wherein the particle is immobilized by freezing a liquid in which the particle is suspended.

23. The method of claim 20, wherein the particle is immobilized by suspending the particle in a polymer resin and curing the resin.

24. The method of claim 1, wherein the particle is obtained from a composition in which particles that comprise the substance are mixed with particles that do not comprise the substance.

25. The method of claim 24, wherein the substance is a pharmaceutically active agent.

26. The method of claim 25, wherein the agent is mixed with an excipient.

27. The method of claim 25, wherein the agent is formulated for aerosol delivery.

28. The method of claim 25, wherein the agent is formulated for parenteral delivery.

29. The method of claim 25, wherein the agent is formulated for oral delivery.

30. The method of claim 25, wherein the agent is formulated for topical delivery.

31. The method of claim 1, wherein the particle is a solid.

32. The method of claim 1, wherein the particle is a first liquid dispersed in a second liquid.

33. The method of claim 32, wherein the particle is selected from the group consisting of an oily liquid droplet in an oil-in-water emulsion and an aqueous liquid droplet in a water-in-oil emulsion.

34. The method of claim 1, wherein the particle is a micelle.

35. A method of assessing a geometric property of a particle of a substance in a sample including multiple particles, the method comprising irradiating the sample, identifying the particle of the substance by assessing Raman-shifted radiation at a Raman shift value characteristic of the substance, generating an optical image of particles in the field, and determining the geometric property of the particle of the substance from the optical image.

36. A method of assessing particles of a first substance and a second substance in a sample, the method comprising irradiating the sample, generating a first image of Raman-shifted radiation scattered from the sample at a Raman shift value characteristic of the first substance, and comparing the first image with a second image of Raman-shifted radiation scattered from the sample at a Raman shift value characteristic of the second substance.

* * * * *